United States Patent
Nagase et al.

(10) Patent No.: US 7,888,401 B2
(45) Date of Patent: Feb. 15, 2011

(54) INK COMPOSITION AND INKJET INK, AND IMAGE-FORMING METHOD AND RECORDED MATERIAL USING THE SAME, AND OXETANE COMPOUND

(75) Inventors: Hisato Nagase, Minami-ashigara (JP); Takehiko Sato, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 736 days.

(21) Appl. No.: 11/878,817

(22) Filed: Jul. 27, 2007

(65) Prior Publication Data

US 2008/0033072 A1 Feb. 7, 2008

(30) Foreign Application Priority Data

Jul. 28, 2006 (JP) .............................. 2006-206308
Jul. 28, 2006 (JP) .............................. 2006-206324

(51) Int. Cl.
*C08F 2/46* (2006.01)
*C08F 2/50* (2006.01)
*C08J 3/28* (2006.01)
*C09D 11/10* (2006.01)
*C09D 11/00* (2006.01)
*C09D 11/02* (2006.01)

(52) U.S. Cl. ...................... 522/169; 522/168; 522/178; 522/181; 522/909; 522/170; 523/160; 523/161; 106/31.13; 106/31.6

(58) Field of Classification Search .................. 522/168, 522/169, 170, 178, 181, 909; 523/160, 161; 106/31.6, 31.13
See application file for complete search history.

(56) References Cited

U.S. PATENT DOCUMENTS 6,979,719 B1 * 12/2005 Hobel et al. .................. 528/26

FOREIGN PATENT DOCUMENTS

| JP | 2679586 | 8/1997 |
| JP | 2000-169552 | 6/2000 |
| JP | 2001-220526 | 8/2001 |
| JP | 2001-222105 | 8/2001 |
| JP | 2002-317139 | 10/2002 |
| JP | 2003-221528 | 8/2003 |
| JP | 2003-221530 | 8/2003 |
| JP | 2003-221532 | 8/2003 |
| JP | 2005171122 A * | 6/2005 |

OTHER PUBLICATIONS

Vuluga et al. Photoinitiated cationic polymerization of 1,3-dioxepane. European Polymer Journal. vol. 35, Issue 12, Dec. 1999, pp. 2193-2195.*

\* cited by examiner

*Primary Examiner*—Sanza L McClendon
(74) *Attorney, Agent, or Firm*—Sughrue Mion, PLLC

(57) ABSTRACT

An active energy ray-curable ink composition, which contains a compound having, in its molecule, an oxetane ring and at least one selected from a dioxolane ring, a dioxane ring, and a dioxepane ring; an ink composition, which contains a cationically-polymerizable compound having, in its molecule, both an oxetane ring and a bicycloorthoester ring; an inkjet ink, which contains the active energy ray-curable ink composition or the ink composition; and an image-forming method and a recorded material, using the inkjet ink; an oxetane compound of a specific structure.

27 Claims, No Drawings

INK COMPOSITION AND INKJET INK, AND IMAGE-FORMING METHOD AND RECORDED MATERIAL USING THE SAME, AND OXETANE COMPOUND

FIELD OF THE INVENTION

The present invention relates to an ink composition (e.g. an active energy ray-curable ink composition) and an inkjet ink, and to an image-forming method and a recorded material using the inkjet ink, and also to an oxetane compound.

BACKGROUND OF THE INVENTION

In recent years, printing with inkjet printers that necessitates no printing plate has been spread to produce a limited number of copies of a recorded material, such as a local ad and a large poster. Inks for use in inkjet printers generally include aqueous type inks, solvent type inks, and ultraviolet-curable type inks. Aqueous type inkjet inks are low in water resistance when printed on standard paper, and can easily cause blurring. When printed on a non-water-absorbing recording medium such as a plastic, aqueous type inkjet inks are poor in fixing ink droplets and thus a failure in image formation is apt to occur. Aqueous type inkjet inks also have the disadvantage that since the drying process for the solvent is very slow, recorded materials immediately after printing have to be dried without being piled up or superposed.

On the other hand, solvent type inks are suitable for printing on a non-water-absorbing recording medium such as a plastic, but have the disadvantages that since the solvent on the medium has to be dried, it takes a certain period of time to perform drying, and that an air-exhausting system or a solvent-collecting equipment for the evaporation of organic solvents also have to be provided.

To solve these problems, inkjet inks that harden and deposit not by volatization of ink solvent but by irradiation of radiation ray were developed. For example, JP-A-2003-221528 ("JP-A" means unexamined published Japanese patent application), JP-A-2003-221532, and JP-A-2003-221530 disclose inks containing a monomer having a polymerizable group and an oil-soluble dye. Alternatively, JP-A-2001-222105 discloses a photopolymerizable composition containing a photopolymerizable compound and a photopolymerization initiator. Since these inks are of a radical polymerization type, however, the polymerization can be inhibited by oxygen, and thus it is apt to cause a failure in curing in the air, on which an improvement has been demanded.

Under the circumstances, there are disclosed inks using cationic polymerization that can be free from oxygen inhibition for polymerization. Known cationically polymerizable monomers that are generally used for cationic polymerization-type ultraviolet-curable type ink, include oxirane ring-containing epoxy compounds, oxetane compounds, and vinyl ether compounds. Specifically, it is known that the polymerization rate can be significantly increased, by using a combination of an epoxy compound and an oxetane compound (Japanese Patent No. 2679586). In particular, oxetane compounds have good heat resistance, adhesive properties, and chemical resistance, and thus are useful for use in combination with reactivity-enhancing epoxy compounds. Concerning cationically polymerizable ink, for example, JP-A-2000-169552, JP-A-2001-220526, and JP-A-2002-317139 disclose active energy ray-curable compositions containing oxirane or oxetane. However, these active energy ray-curable compositions have insufficient curing property, and thus the resultant cured products may be brittle and insufficient in adhesion to a recording medium. Further, JP-A-2002-317139 discloses an active energy ray-curable composition containing oxirane, oxetane, or vinyl ether. Although the active energy ray-curable composition has relatively good curing property, the resultant cured product may be brittle and insufficient in the adhesion, and the active energy ray-curable composition generates a bad smell, and thus the development of highly sensitive materials without using vinyl ether has been demanded. The ink compositions as disclosed in these patents documents have a problem in which since their curing property is not sufficient, a high-illumination-intensity ultraviolet lamp is necessary, to make the printing apparatus large in size and complicated.

SUMMARY OF THE INVENTION

The present invention resides in an active energy ray-curable ink composition, which comprises a compound having, in its molecule, an oxetane ring and at least one selected from a dioxolane ring, a dioxane ring, and a dioxepane ring. Further, the present invention resides in an inkjet ink, which comprises the active energy ray-curable ink composition. Further, the present invention resides in an image-forming method, which comprises the step of: recording an image by inkjet-recording of ejecting the active energy ray-curable inkjet ink. Further, the present invention resides in a recorded material, which is formed by using the active energy ray-curable inkjet ink.

Further, the present invention resides in an ink composition, which comprises a cationically-polymerizable compound having, in its molecule, both an oxetane ring and a bicycloorthoester ring. Further, the present invention resides in an inkjet-recording ink, which comprises the ink composition. Further, the present invention resides in an image-forming method, which comprises the step of: recording an image by inkjet-recording of ejecting the inkjet-recording ink. Further, the present invention resides in a recorded material, which is formed by using the inkjet-recording ink. Further, the present invention resides in an oxetane compound represented by formula (2-I):

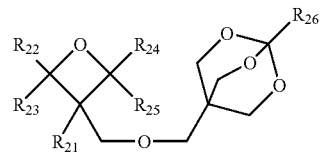

Formula (2-I)

wherein $R_{21}$ to $R_{26}$ each independently represent a hydrogen atom or a substituent.

Other and further features and advantages of the invention will appear more fully from the following description.

DETAILED DESCRIPTION OF THE INVENTION

According to the present invention, there is provided the following means:

(1) An active energy ray-curable ink composition, comprising a compound having, in its molecule, an oxetane ring and at least one selected from a dioxolane ring, a dioxane ring, and a dioxepane ring;

(2) The active energy ray-curable ink composition according to Item (1), wherein the compound contains, per molecule, one oxetane ring and any one of a dioxolane ring, a dioxane ring or a dioxepane ring;

(3) The active energy ray-curable ink composition according to Item (1) or (2), further comprising any one of an oxirane ring-containing compound or an oxetane ring-containing compound;

(4) The active energy ray-curable ink composition according to any one of Items (1) to (3), further comprising at least one polymerization initiator and at least one photosensitizer;

(5) The active energy ray-curable ink composition according to any one of Items (1) to (4), whose viscosity at 25° C. is 2 to 20 mPa·s;

(6) An inkjet ink, comprising the active energy ray-curable ink composition according to any one of Items (1) to (5);

(7) An image-forming method, comprising:

an image-recording step to record an image by inkjet-recording of ejecting (or discharging) the active energy ray-curable inkjet ink according to Item (6);

(8) The image-forming method according to Item (7), which comprises: the image-recording step of recording said image on a recording material with the active energy ray-curable inkjet ink; and an image-curing step of curing the image recorded on the recording material in the image-recording step by irradiating the image with an active energy ray;

(9) The image-forming method according to Item (8), wherein a light-emitting diode or a semiconductor laser is a light source for the irradiation with the active energy ray;

(10) The image-forming method according to Item (8) or (9), wherein the central wavelength of the active energy ray is 365±20 nm;

(11) The image-forming method according to any one of Items (8) to (10), wherein the thickness of the image cured in the image-curing step is 2 to 30 μm;

(12) A recorded material, which is formed by using the active energy ray-curable inkjet ink according to Item (6);

(13) An ink composition, comprising a cationically-polymerizable compound having, in its molecule, both an oxetane ring and a bicycloorthoester ring;

(14) The ink composition according to Item (13), wherein the cationically-polymerizable compound is a compound having one oxetane ring and one bicycloorthoester ring in its molecule;

(15) The ink composition according to Item (13) or (14), wherein the cationically-polymerizable compound is a compound in which one oxetane ring and one bicycloorthoester ring are linked together via an ether bond;

(16) The ink composition according to any one of Items (13) to (15), further comprising any one of an oxirane ring-containing compound or an oxetane ring-containing compound;

(17) The ink composition according to any one of Items (13) to (16), further comprising at least one polymerization initiator and at least one photosensitizer;

(18) The ink composition according to any one of Items (13) to (17), whose viscosity at 25° C. is 2 to 20 mPa·s;

(19) An inkjet-recording ink, comprising the ink composition according to any one of Items (13) to (18);

(20) An image-forming method, comprising:

an image-recording step to record an image by inkjet-recording of ejecting (or discharging) the inkjet-recording ink according to Item (19);

(21) The image-forming method according to Item (20), which comprises: the image-recording step of recording said image on a recording material with the inkjet-recording ink; and an image-curing step of curing the image recorded on the recording material in the image-recording step by irradiating the image with an active energy ray;

(22) The image-forming method according to Item (21), wherein a light-emitting diode or a semiconductor laser is a light source for the irradiation with the active energy ray;

(23) The image-forming method according to Item (21) or (22), wherein the central wavelength of the active energy ray is 365±20 nm;

(24) The image-forming method according to any one of Items (21) to (23), wherein the thickness of the image cured in the image-curing step is 2 to 30 μm;

(25) A recorded material, which is formed by using the inkjet-recording ink according to Item (19);

(26) An oxetane compound represented by formula (2-I):

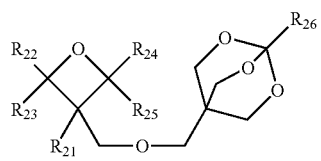

Formula (2-I)

wherein $R_{21}$ to $R_{26}$ each independently represent a hydrogen atom or a substituent; and

(27) The oxetane compound according to Item (26), wherein the compound represented by formula (2-I) is a compound represented by formula (2-II):

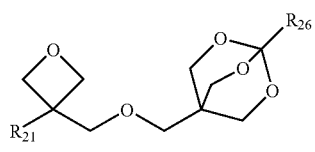

Formula (2-II)

wherein $R_{21}$ and $R_{26}$ each independently represent a hydrogen atom or a substituent.

Hereinafter, a first embodiment of the present invention means to include the active energy ray-curable ink composition, as described in the Items (1) to (5) above; the inkjet ink, as described in the Item (6) above; the image-forming method, as described in the Items (7) to (11) above; and the recorded material, as described in the Item (12) above.

Further, a first embodiment of the present invention means to include the ink composition, as described in the Items (13) to (18) above; the inkjet-recording ink, as described in the Item (19) above; the image-forming method, as described in the Items (20) to (24) above; and the recorded material, as described in the Item (25) above; the oxetane compound, as described in the Items (26) to (27) above.

Herein, the present invention means to include both of the above first and second embodiments, unless otherwise specified.

Herein, in the present invention, the term "ejection stability" refers to the ability to stably continue the ejection of inkjet ink without causing any ejection failure by nozzle clogging.

Herein, the rings of dioxolane, dioxane, and dioxepane are collectively referred to as "two oxygen atoms-containing heterocycles".

Hereinafter, the present invention will be described in detail.

The first embodiment of the present invention will be described in detail below.

The active energy ray-curable ink composition of the first embodiment of the present invention is preferably used as an inkjet ink, and a feature thereof resides in containing a compound having an oxetane ring and any of a dioxolane ring, a dioxane ring, or a dioxepane ring, in its molecule.

The compound for use in the first embodiment of the present invention, that has an oxetane ring and a dioxolane, dioxane or dioxepane ring in its molecule, is preferably represented by formula (I), (II), or (III).

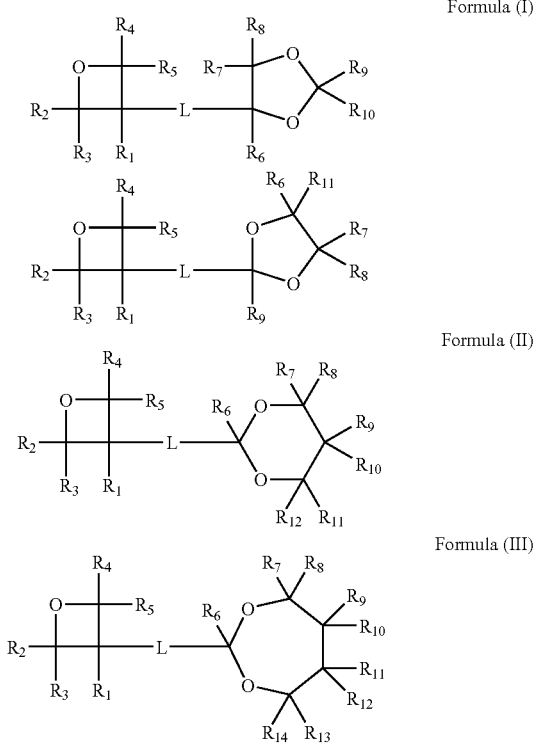

In formulae (I) to (III), $R_1$ to $R_{14}$ each independently represent a hydrogen atom or a substituent. Examples of the substituent include an alkyl group, an alkenyl group, an alkynyl group, an aromatic hydrocarbon group, a heteroaromatic group, a heterocyclic group, an alkoxy group, an aryloxy group, an alkylthio group, an arylthio group, an alkoxycarbonyl group, an aryloxycarbonyl group, a sulfamoyl group, an acyl group, an acyloxy group, an amido group, a carbamoyl group, a ureido group, an alkylsulfonyl group, an arylsulfonyl group, an amino group, a halogen atom, a fluorinated hydrocarbon group, a cyano group, a nitro group, a hydroxy group, a mercapto group, and a silyl group. These substituents may be further substituted with any of the above substituents, and two or more of these substituents may bond to one another, to form a ring. Alternatively, the ends of any two groups of $R_1$ to $R_{14}$ may be arbitrarily bonded, to form a ring. Each of these rings is preferably an aliphatic hydrocarbon ring, and the ring may be substituted with any of the above-mentioned substituents. $R_1$ to $R_{14}$ are each preferably a hydrogen atom or an alkyl group.

In formulas (I) to (III), the alkyl group represented by $R_1$ to $R_{14}$ may be linear, branched, or cyclic. Examples of the alkyl group include a methyl group, an ethyl group, a propyl group, an isopropyl group, a t-butyl group, a pentyl group, a hexyl group, an octyl group, a dodecyl group, a tridecyl group, a tetradecyl group, a pentadecyl group, a cyclopentyl group, and a cyclohexyl group. The alkyl group is preferably an alkyl group having 1 to 3 carbon atoms, more preferably a methyl group or an ethyl group, and particularly preferably a methyl group.

In formulas (I) to (III), examples of the alkenyl group represented by $R_1$ to $R_{14}$ include a vinyl group and an allyl group. Examples of the alkynyl group include an ethynyl group and a propargyl group. Examples of the aromatic hydrocarbon group include a phenyl group, a 4-methoxyphenyl group, and a naphthyl group. Examples of the heteroaromatic group include a furyl group, a thienyl group, a pyridyl group, a pyridazyl group, a pyrimidyl group, a pyrazyl, triazyl group, an imidazolyl group, a pyrazolyl group, a thiazolyl group, a benzimidazolyl group, a benzoxazolyl group, a quinazolyl group, and a phthalazyl group. Examples of the heterocyclic group include a pyrrolidyl group, an imidazolidyl group, a morpholyl group, and an oxazolidyl group. Examples of the alkoxy group include a methoxy group, an ethoxy group, a propyloxy group, a pentyloxy group, a hexyloxy group, an octyloxy group, and a dodecyloxy group. Examples of the aryloxy group include a phenoxy group and a naphthyloxy group. Examples of the alkylthio group include a methylthio group, an ethylthio group, a propylthio group, a pentylthio group, a hexylthio group, an octylthio group, and a dodecylthio group. Examples of the arylthio group include a phenylthio group and a naphthylthio group, Examples of the alkoxycarbonyl group include a methyloxycarbonyl group, an ethyloxycarbonyl group, a butyloxycarbonyl group, an octyloxycarbonyl group, and a dodecyloxycarbonyl group. Examples of the aryloxycarbonyl group include a phenyloxycarbonyl group and a naphthyloxycarbonyl group. Examples of the sulfamoyl group include an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group, and a 2-pyridylaminosulfonyl group. Examples of the acyl group include an acetyl group, an ethylcarbonyl group, a propylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, and a pyridylcarbonyl group. Examples of the acyloxy group include an acetyloxy group, an ethylcarbonyloxy group, a butylcarbonyloxy group, an octylcarbonyloxy group, a dodecylcarbonyloxy group, and a phenylcarbonyloxy group, Examples of the amido group include a methylcarbonylamino group, an ethylcarbonylamino group, a dimethylcarbonylamino group, a propylcarbonylamino group, a pentylcarbonylamino group, a cyclohexylcarbonylamino group, a 2-ethylhexylcarbonylamino group, an octylcarbonylamino group, a dodecylcarbonylamino group, a phenylcarbonylamino group, and a naphthylcarbonylamino group. Examples of the carbamoyl group include an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethylhexylaminocarbonyl group, a dodecylaminocarbonyl group, a phenylaminocarbonyl group, a naphthylaminocarbonyl group, and a 2-pyridylaminocarbonyl group. Examples of the ureido group include a methylureido group, an ethylureido group, a pentylureido group, a cyclohexylureido group, an octylureido group, a dodecylureido group, a phenylureido group, a naphthylureido group, and a 2-pyridylaminoureido group, Examples of the alkylsulfonyl group include a methylsulfonyl group, an ethylsulfonyl group, a butylsulfonyl group, a cyclohexylsulfonyl group, a 2-ethylhexylsulfonyl group, and a dodecylsulfonyl group. Examples of the arylsulfonyl group include a phenylsulfonyl group, a naphthylsulfonyl group, and a 2-pyridylsulfonyl group. Examples of the amino group include an amino group, an ethylamino group, a dimethylamino group, a butylamino group, a cyclopentylamino group, a 2-ethylhexylamino group, a dodecylamino group, an anilino group, a naphthylamino group, and a 2-pyridylamino group. Examples of the halogen atom include a fluorine atom, a chlorine atom, and a bromine atom. Examples of the fluorinated hydrocarbon group include a fluoromethyl group, a trifluoromethyl group, a pentafluoroethyl group, and a pentafluorophenyl group. Examples of the silyl group include a trimethylsilyl group, a triisopropylsilyl group, a triphenylsilyl group, and a phenyldiethylsilyl group.

In formulae (I) to (III), L represents a divalent linking group, examples of which include a linking group having 1 to 30 carbon atoms, preferably a linking group having 1 to 25 carbon atoms, particularly preferably a linking group having 1 to 20 carbon atoms. Examples of the linking group include those having at least one structure selected from an aliphatic group, an aromatic group, an ether bond, a thioether bond, a carbonyl group, and an ester group. The linking group is preferably a linear or branched alkylene group, or an alkylene group containing an ether bond; and specific examples thereof include —(CH$_2$)$_2$—, —(CH$_2$)$_3$—, —(CH$_2$)$_4$—, —(CH$_2$)$_6$—, —(CH$_2$)$_8$—, —(CH$_2$)$_{12}$—, —CH$_2$OCH$_2$—, —CH$_2$CH$_2$OCH$_2$CH$_2$—, —CH$_2$OCH$_2$CH$_2$OCH$_2$—, —CH$_2$OCH$_2$CH$_2$CH$_2$OCH$_2$—, —CH$_2$OCH$_2$CH$_2$CH$_2$CH$_2$OCH$_2$—, —CH$_2$OCH$_2$CH$_2$CH$_2$CH$_2$CH$_2$CH$_2$CH$_2$CH$_2$OCH$_2$—, —CH$_2$OCH$_2$CH$_2$OCH$_2$CH$_2$OCH$_2$—, —CH$_2$OCH(CH$_3$)CH$_2$OCH$_2$—, —CH$_2$OCH(CH$_3$)CH$_2$OCH(CH$_3$)CH$_2$OCH$_2$—, —CH$_2$OCH(CH$_3$)CH$_2$CH$_2$OCH$_2$—, —CH$_2$OCH(CH$_3$)CH$_2$CH$_2$OCH$_2$—, —CH$_2$OCH$_2$C(CH$_3$)$_2$CH$_2$OCH$_2$—, —CH$_2$OCH$_2$CH=CHCH$_2$OCH$_2$—, —CH$_2$OCH$_2$CH=C(CH$_3$)CH$_2$CH=C(CH$_3$)CH$_2$OCH$_2$—, —CH$_2$SCH$_2$—, —CH$_2$OCH$_2$CH$_2$SCH$_2$CH$_2$OCH$_2$—,

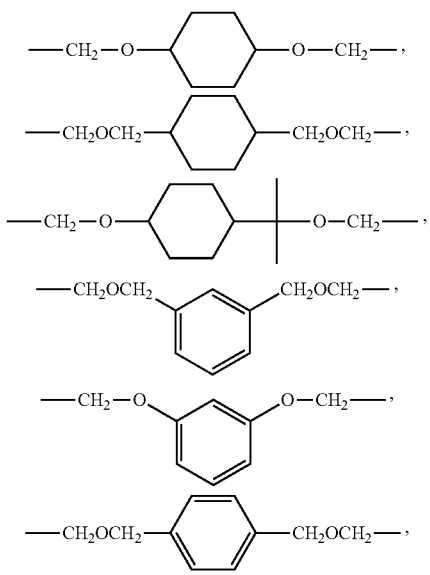

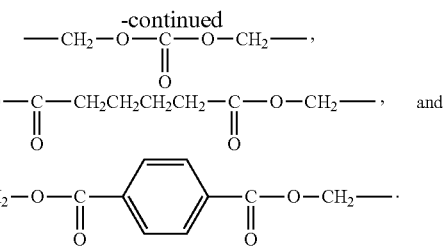

In the compound for use in the ink composition of the first embodiment of the present invention, having an oxetane ring and any of a dioxolane, dioxane, or dioxepane ring in its molecule, the oxetane ring may have an alkyl group or/and an aryl group as a substituent(s) thereon. The alkyl group may be linear, branched, or cyclic; and examples thereof include a methyl group, an ethyl group, a propyl group, an isopropyl group, a tert-butyl group, a pentyl group, a hexyl group, an octyl group, a dodecyl group, a tridecyl group, a tetradecyl group, a pentadecyl group, a cyclopentyl group, and a cyclohexyl group; and the alkyl group is preferably an alkyl group having 1 to 3 carbon atoms, more preferably a methyl group or an ethyl group.

Examples of the aryl group include a phenyl group, a 4-methoxyphenyl group, and a naphthyl group, with preference given to a phenyl group.

In the compound for use in the first embodiment of the present invention having an oxetane ring and a dioxolane ring in its molecule, the dioxolane ring is preferably 1,3-dioxolane and may have an alkyl group or/and an aryl group as a substituent(s) thereon. Preferred examples of the alkyl group and aryl group have the same meanings as the aforementioned preferred examples of the group(s) as a substituent(s) on the oxetane ring.

In the compound for use in the first embodiment of the present invention having an oxetane ring and a dioxane ring in its molecule, the dioxane ring is preferably 1,3-dioxane and may have an alkyl group or/and an aryl group as a substituent(s) thereon. Preferred examples of the alkyl group and aryl group have the same meanings as the aforementioned preferred examples of the group(s) as a substituent(s) on the oxetane ring.

In the compound for use in the first embodiment of the present invention having an oxetane ring and a dioxepane ring in its molecule, the dioxepane ring is preferably 1,3-dioxepane and may have an alkyl group or/and an aryl group as a substituent(s) thereon. Preferred examples of the alkyl group and aryl group have the same meanings as the aforementioned preferred examples of the group(s) as a substituent(s) on the oxetane ring.

The oxetane ring is preferably linked through an appropriate substituent at the 3-position of the oxetane to the dioxolane, dioxane or dioxepane ring. The linking group is preferably an alkylene group containing an ether bond.

Specific examples of the compound for use in the first embodiment of the present invention, having an oxetane ring and any of a dioxolane, dioxane, or dioxepane ring in its molecule, are shown below, but the present invention is not meant to be limited to those.

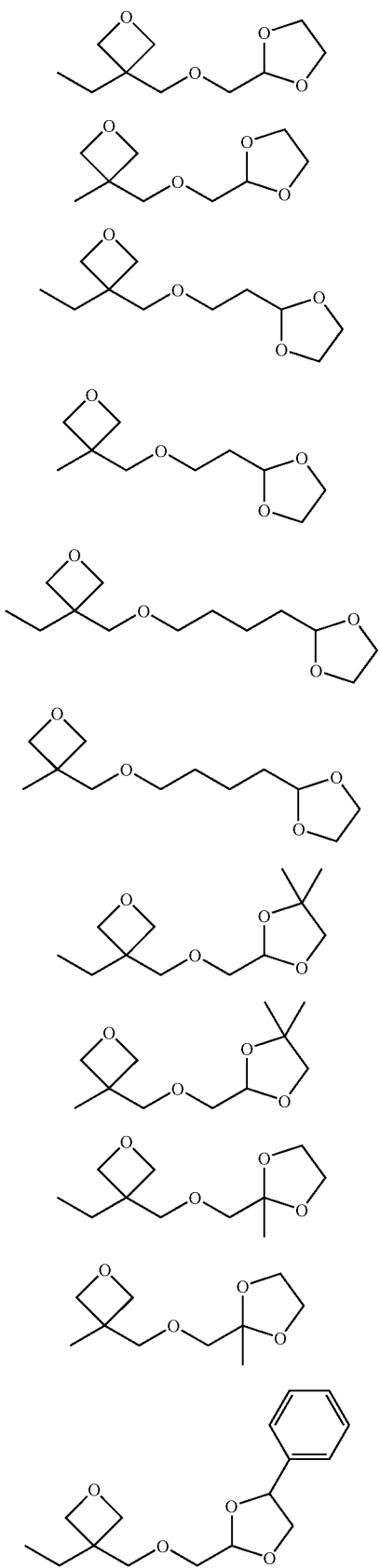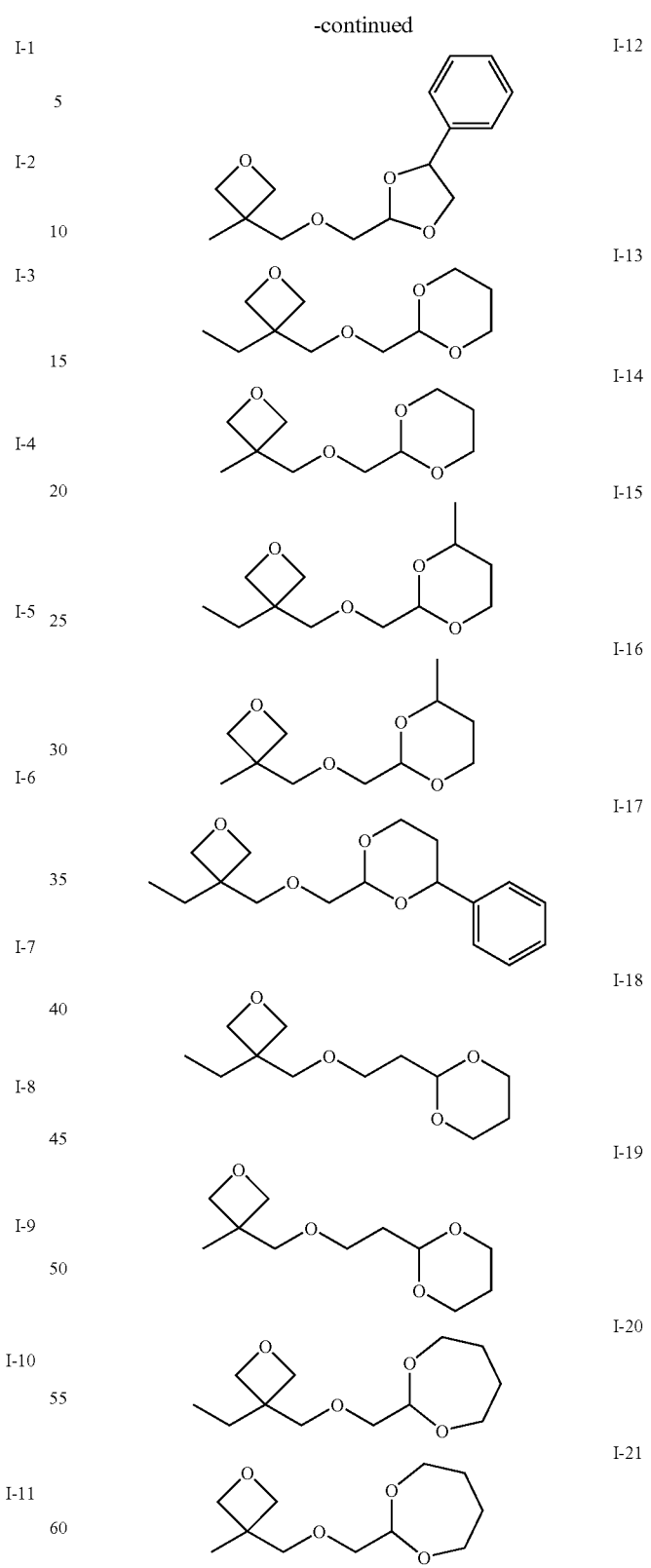
The second embodiment of the present invention will be described in detail below.
A feature of the ink composition of the second embodiment of the present invention resides in containing a cationically-polymerizable compound having both an oxetane ring and a bicycloorthoester ring in its molecule.

The bicycloorthoester ring group of the cationically-polymerizable compound preferably has 5 to 20 carbon atoms, more preferably 5 to 15 carbon atoms. Preferred specific examples of the bicycloorthoester ring include 2,6,7-trioxabicyclo[2,2,2]penta-4-yl. Further, the bicycloorthoester ring may be substituted at the 1-position with a substituent (preferably an alkyl group) as described in the below, and thus another preferred examples include 1-methyl-2,6,7-trioxabicyclo[2,2,2]penta-4-yl.

In the cationically-polymerizable compound for use in the second embodiment of the present invention, having both an oxetane ring and a bicycloorthoester ring in its molecule, the oxetane ring may have a substituent(s) thereon. Examples of the substituent include an alkyl group, an alkenyl group, an alkynyl group, an aromatic hydrocarbon group, a heteroaromatic group, a heterocyclic group, an alkoxy group, an aryloxy group, an alkylthio group, an arylthio group, an alkoxycarbonyl group, an aryloxycarbonyl group, a sulfamoyl group, an acyl group, an acyloxy group, an amido group, a carbamoyl group, a ureido group, an alkylsulfonyl group, an arylsulfonyl group, an amino group, a halogen atom, a fluorinated hydrocarbon group, a cyano group, a nitro group, a hydroxy group, a mercapto group, and a silyl group. These substituents may be further substituted with any of the above substituents, and two or more of these substituents may bond to one another, to form a ring. Preferred examples of the group on the oxetane ring have the same meanings as the aforementioned examples of the preferred group(s) represented by any of $R_1$ to $R_{14}$ in formulas (I) to (III).

In the cationically-polymerizable compound for use in the second embodiment of the present invention having both an oxetane ring and a bicycloorthoester ring in its molecule, the bicycloorthoester ring may have an alkyl group or/and an aryl group as a substituent(s) thereon. Preferred examples of the alkyl group and aryl group have the same meanings as the aforementioned preferred examples of the substituent on the oxetane ring.

The oxetane ring and the bicycloorthoester ring are preferably linked by an ether bond-containing alkylene linking group as a linking group, and the bicycloorthoester ring is particularly preferably linked at the 3-position of the oxetane.

The cationically-polymerizable compound is preferably an oxetane compound represented by formula (2-I).

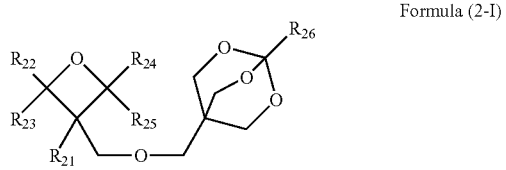

Formula (2-I)

In formula (2-II), $R_{21}$ to $R_{26}$ each independently represent a hydrogen atom or a substituent.

In the above formula, $R_{21}$ to $R_{26}$ each independently represent a hydrogen atom or a substituent. Examples of the substituent include an alkyl group, an alkenyl group, an alkynyl group, an aromatic hydrocarbon group, a heteroaromatic group, a heterocyclic group, an alkoxy group, an aryloxy group, an alkylthio group, an arylthio group, an alkoxycarbonyl group, an aryloxycarbonyl group, a sulfamoyl group, an acyl group, an acyloxy group, an amido group, a carbamoyl group, a ureido group, an alkylsulfonyl group, an arylsulfonyl group, an amino group, a halogen atom, a fluorinated hydrocarbon group, a cyano group, a nitro group, a hydroxy group, a mercapto group, and a silyl group. These substituents may be further substituted with any of the above substituents, and two or more of these substituents may bond to one another, to form a ring. Alternatively, the ends of any two groups of $R_{21}$ to $R_{25}$ may be arbitrarily bonded, to form a ring. Each of these rings is preferably an aliphatic hydrocarbon ring, and the ring may be substituted with any of the above-mentioned substituents. $R_{21}$ to $R_{26}$ are each preferably a hydrogen atom or an alkyl group. Preferred examples of the group represented by any of $R_{21}$ to $R_{26}$ in formula (2-I) have the same meanings as the aforementioned examples of the preferred group(s) represented by any of $R_1$ to $R_{14}$ in formulas (I) to (III).

The compound represented by formula (2-I) is more preferably a compound represented by formula (2-II).

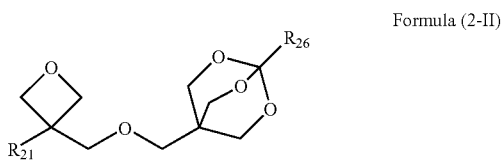

Formula (2-II)

In the formula, $R_{21}$ and $R_{26}$ each independently represent a hydrogen atom or a substituent.

In formula (2-II), $R_{21}$ and $R_{26}$ have the same meanings as those in formula (2-I), respectively, and the preferable ranges thereof are also the same.

Specific examples of the compound for use in the second embodiment of the present invention, as represented by formula (2-I) or (2-II), are shown below, but the present invention is not meant to be limited to those.

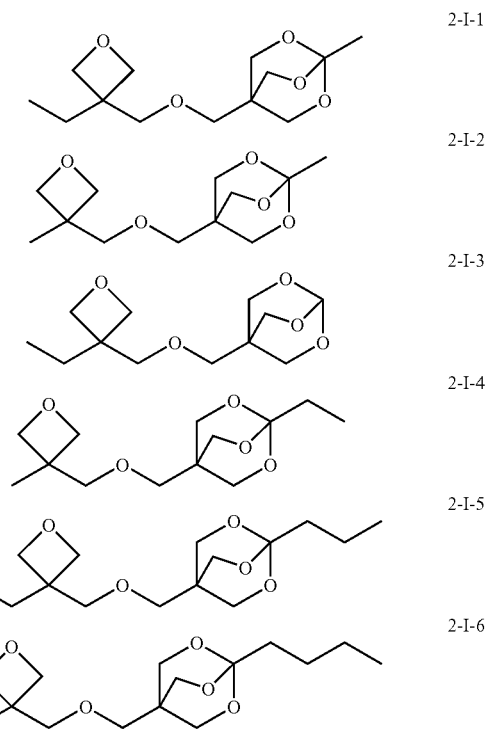

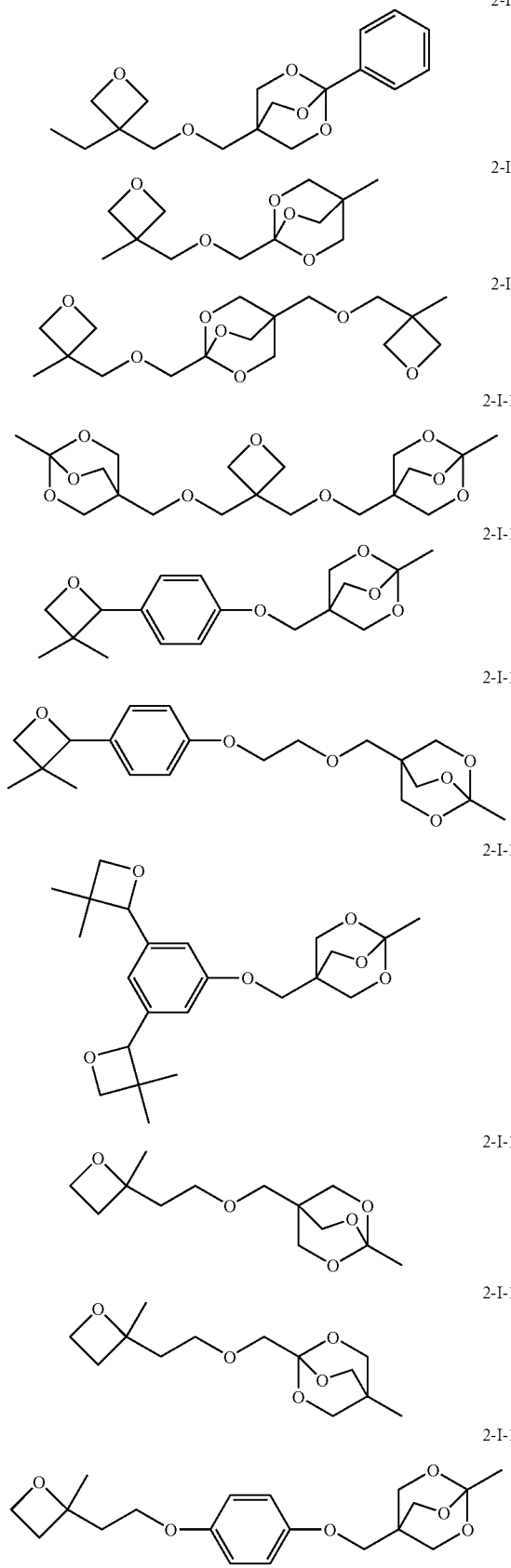
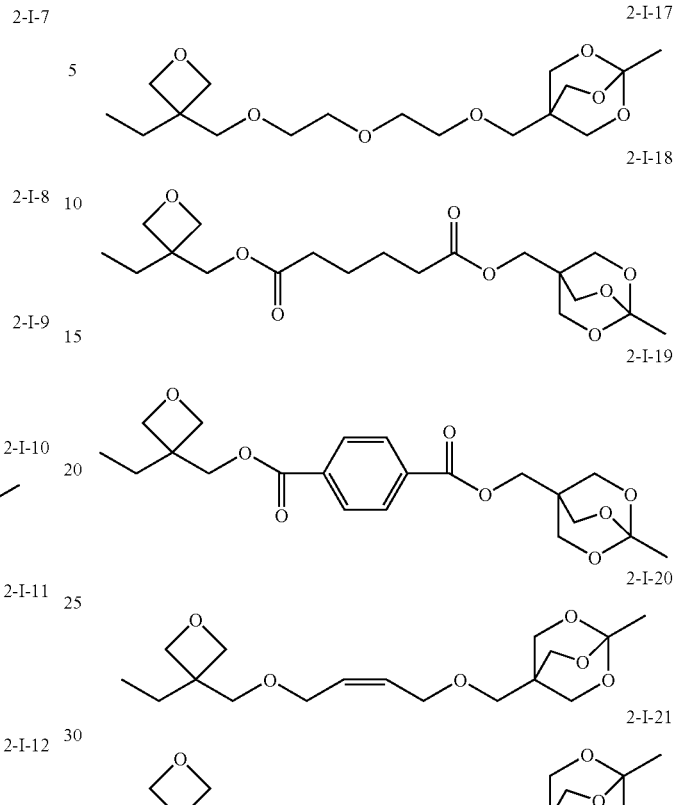

The compound for use in the present invention, i.e. in the first embodiment or/and the second embodiment of the present invention, may be synthesized by known synthetic methods, such as those disclosed, for example, in JP-A-6-16804, Japanese Patent No. 3403354, and J. Am. Chem. Soc., 1957, 79. A typical synthetic example is described below. Hereinafter, the "compound for use in the present invention" means to include both the compound, as defined in Item (1) above, having in its molecule the oxetane ring and the specific two oxygen atoms-containing heterocycle, for use in the first embodiment of the present invention, and the compound represented by formula (2-I) or (2-II), for use in the second embodiment of the present invention.

SYNTHETIC EXAMPLE OF COMPOUND I-1

In 100 mL of DMF, 6.0 g of sodium hydride was dispersed under ice cooling, and 11.6 g of 3-ethyl-3-oxetanemethanol was added dropwise thereto. After stirring for 30 minutes, 15.0 g of 4-chloromethyl-2,2-dimethyl-1,3-dioxolane was added dropwise thereto. After stirring for 30 minutes, the mixture was heated to room temperature and then stirred for 4 hours. The reaction liquid was poured into water and extracted with ethyl acetate. The ethyl acetate layer was washed with water and with an aqueous saturated sodium chloride solution and then dried over magnesium sulfate. The ethyl acetate was removed by distillation, and the residue was purified by column chromatography, to give Compound I-1.

$^1$H-NMR (300 MHz, CDCl$_3$, δ): 4.46 (d, 2H), 4.38 (d, 2H), 4.27 (m, 1H), 4.06 (m, 1H), 3.79 (m, 1H), 3.64-3.50 (m, 4H), 1.76 (q, 2H), 1.43 (s, 3H), 1.37 (s, 3H), 0.84 (t, 3H)

SYNTHETIC EXAMPLE OF COMPOUND I-3

In 100 mL of DMF, 6.0 g of sodium hydride was dispersed under ice cooling, and 11.6 g of 3-ethyl-3-oxetanemethanol was added dropwise thereto. After stirring for 30 minutes, 16.7 g of 2-bromomethyl-1,3-dioxolane was added dropwise thereto. After stirring for 30 minutes, the mixture was heated to room temperature and then stirred for 8 hours. The reaction liquid was poured into water and extracted with ethyl acetate. The ethyl acetate layer was washed with water and with an aqueous saturated sodium chloride solution and then dried over magnesium sulfate. The ethyl acetate was removed by distillation, and the residue was purified by column chromatography, to give Compound I-3.

$^1$H-NMR (300 MHz, CDCl$_3$, δ): 5.06 (t, 1H), 4.45 (d, 2H), 4.38 (d, 2H), 3.97 (m, 4H), 3.66 (s, 2H), 3.58 (d, 2H), 1.77 (q, 2H), 0.86 (t, 3H)

SYNTHETIC EXAMPLE OF COMPOUND I-7)

In 100 mL of DMF, 6.0 g of sodium hydride was dispersed under ice cooling, and 11.6 g of 3-ethyl-3-oxetanemethanol was added dropwise thereto. After stirring for 30 minutes, 18.1 g of 2-(2-bromoethyl)-1,3-dioxolane was added dropwise thereto. After stirring for 30 minutes, the mixture was heated to room temperature and then stirred for 8 hours. The reaction liquid was poured into water and extracted with ethyl acetate. The ethyl acetate layer was washed with water and with an aqueous saturated sodium chloride solution and then dried over magnesium sulfate. The ethyl acetate was removed by distillation, and the residue was purified by column chromatography, to give Compound I-7.

$^1$H-NMR (300 MHz, CDCl$_3$, δ): 5.00 (t, 1H), 4.45 (d, 2H), 4.38 (d, 2H), 3.98 (m, 2H), 3.88 (m, 2H), 3.61 (t, 2H), 3.55 (s, 2H), 1.98 (m, 2H), 1.76 (q, 2H), 0.86 (t, 3H)

SYNTHETIC EXAMPLE OF COMPOUND I-18

In 100 mL of DMF, 6.0 g of sodium hydride was dispersed under ice cooling, and 11.6 g of 3-ethyl-3-oxetanemethanol was added dropwise thereto. After stirring for 30 minutes, 19.5 g of 2-(2-bromoethyl)-1,3-dioxane was added dropwise thereto. After stirring for 30 minutes, the mixture was heated to room temperature and then stirred for 6 hours. The reaction liquid was poured into water and extracted with ethyl acetate. The ethyl acetate layer was washed with water and with an aqueous saturated sodium chloride solution and then dried over magnesium sulfate. The ethyl acetate was removed by distillation, and the residue was purified by column chromatography, to give Compound I-18.

$^1$H-NMR (300 MHz, CDCl$_3$, δ): 4.66 (t, 1H), 4.45 (d, 2H), 4.38 (d, 2H), 4.10 (m, 2H), 3.78 (m, 2H), 3.56 (t, 2H), 3.50 (s, 2H), 2.06 (m, 1H), 1.86 (m, 2H), 1.76 (q, 2H), 1.36 (m, 1H), 0.87 (t, 3H)

SYNTHETIC EXAMPLE OF COMPOUND 2-I-1

In an ice bath, 25.6 g of 3-ethyl-3-oxetanemethanol and 100 mL of pyridine were stirred, and 46.1 g of p-toluenesulfonyl chloride was added in separated small portions thereto. After stirring for 3 hours in the ice bath, 500 mL of water was added to the reaction liquid and extraction with ethyl acetate was performed. The ethyl acetate layer was washed with water and with an aqueous saturated sodium chloride solution and then dried over magnesium sulfate. The ethyl acetate was removed by distillation, to give a tosyl derivative of 3-ethyl-3-oxetanemethanol. The yield was 57.6 g (97%).

In 10 mL of toluene, 13.6 g of pentaerythritol, 16.2 g of ortho-triethyl acetate, and 50 mg of p-toluenesulfonic acid monohydrate were dispersed and heated while ethanol generated at 80° C. to 100° C. was removed. After a theoretical amount of ethanol was recovered in 8 hours, the mixture was heated to 125° C. so that toluene was removed by distillation. The residue was mixed with 27.0 g of the tosyl derivative of 3-ethyl-3-oxetanemethanol, and thereto were added 1 g of tributylammonium chloride and 100 ml of dimethylsulfoxide, followed by stirring under cooling with water, and then 14.0 g of potassium tert-butoxide was added in separated small portions thereto. After stirring at room temperature for 4 hours, water was added to the reaction liquid, and extraction with ethyl acetate was performed. The ethyl acetate layer was washed with water and with an aqueous saturated sodium chloride solution and then dried over magnesium sulfate. The ethyl acetate was removed by distillation, and the residue was purified by column chromatography, to give 16.2 g of Compound 2-I-1. The yield was 63%.

$^1$H-NMR (300 MHz, CDCl$_3$, δ): 4.39 (s, 4H), 4.00 (s, 6H), 3.48 (s, 2H), 3.25 (s, 2H), 1.77 (q, 2H), 1.48 (s, 3H), 0.85 (t, 3H)

SYNTHETIC EXAMPLE OF COMPOUND 2-I-2

In an ice bath, 204.3 g of 3-ethyl-3-oxetanemethanol and 500 mL of pyridine were stirred, and 419.4 g of p-toluenesulfonyl chloride was added in separated small portions thereto. After stirring for 3 hours in the ice bath, 2 L of water was added to the reaction liquid, and crystallization was performed. The resultant white solid was separated by filtration and washed with water until the pyridine odor was eliminated, and then dried, to give a tosyl derivative of 3-methyl-3-oxetanemethanol. The yield was 471.9 g (92%).

In 10 mL of toluene, 13.6 g of pentaerythritol, 16.2 g of ortho-triethyl acetate, and 50 mg of p-toluenesulfonic acid monohydrate were dispersed and heated while ethanol generated at 80° C. to 100° C. was removed. After a theoretical amount of ethanol was recovered in 8 hours, the mixture was heated to 125° C. so that toluene was removed by distillation. The residue was mixed with 25.6 g of the tosyl derivative of 3-methyl-3-oxetanemethanol, and thereto were added 1 g of tributylammonium chloride and 100 ml of dimethylsulfoxide, followed by stirring under cooling with water, and then 14.0 g of potassium tert-butoxide was added in separated small portions thereto. After stirring at room temperature for 4 hours, water was added to the reaction liquid, and extraction with ethyl acetate was performed. The ethyl acetate layer was washed with water and with an aqueous saturated sodium chloride solution and then dried over magnesium sulfate. The ethyl acetate was removed by distillation, and the residue was purified by column chromatography, to give 15.0 g of Compound 2-I-2. The yield was 63%.

$^1$H-NMR (300 MHz, CDCl$_3$, δ): 4.45 (d, 2H), 4.38 (d, 2H), 4.02 (s, 6H), 3.44 (s, 2H), 3.24 (s, 2H), 1.45 (s, 3H), 1.30 (s, 3H).

In the composition of the first embodiment of the present invention, the content of the compound, as defined in Item (1) above, having in its molecule the oxetane ring and the specific two oxygen atoms-containing heterocycle, may be arbitrarily set, but it is preferably from 3% by mass to 50% by mass, more preferably from 5% by mass to 40% by mass, based on the total amount of the active energy ray-curable inkjet ink, from the viewpoints of viscosity and curing property.

The compound for use in the first embodiment of the present invention may be used singly or as a mixture of two or more types thereof, or it may be used in combination with another cationically-polymerizable compound(s) different from the compound for use in the first embodiment of the present invention. The sum of the amounts of the compound for use in the first embodiment of the present invention and the another cationically-polymerizable compound(s) is preferably from 70% by mass to 99% by mass, more preferably from 75% by mass to 98% by mass, most preferably from 80% by mass to 95% by mass, based on the total amount of the ink composition.

The ratio of the amount of the compound for use in the first embodiment of the present invention, to the total amount of the polymerizable compounds may be arbitrarily set, but the ratio is preferably from 3% by mass to 60% by mass, more preferably from 5% by mass to 40% by mass, particularly preferably from 10% by mass to 35% by mass, from the viewpoints of curing property, viscosity, as well as the physical properties of the resultant cured product.

In the ink composition of the second embodiment of the present invention, the content of the compound represented by formula (2-I) or (2-II) may be arbitrarily set, but it is preferably from 3% by mass to 50% by mass, more preferably from 5% by mass to 30% by mass, based on the total amount of the ink composition, from the viewpoints of viscosity and curing property.

The compound represented by formula (2-I) or (2-II) for use in the second embodiment of the present invention may be used singly or as a mixture of two or more types thereof, or it may be used in combination with another cationically-polymerizable compound(s) different from the compound for use in the second embodiment of the present invention. The sum of the amounts of the compound for use in the second embodiment of the present invention as represented by formula (2-I) or (2-II) and the another cationically-polymerizable compound(s) is preferably from 70% by mass to 99% by mass, more preferably from 75% by mass to 98% by mass, most preferably from 80% by mass to 95% by mass, based on the total amount of the ink composition.

The ratio of the amount of the compound represented by formula (2-I) or (2-II) for use in the second embodiment of the present invention, to the total amount of the polymerizable compounds may be arbitrarily set, but the ratio is preferably from 3% by mass to 50% by mass, more preferably from 4% by mass to 40% by mass, particularly preferably from 5% by mass to 30% by mass, from the viewpoints of curing property, viscosity, as well as the physical properties of the resultant cured product.

In the following, the constituent features and other conditions common to the first and the second embodiments of the present invention will be explained.

The compound according to the present invention may be used in combination with another cationically-polymerizable compound. As such a compound, any generally known compound having a cationically-polymerizable group may be used, whether it is a monomer, oligomer, or polymer type. Examples of the cationically-polymerizable compound include, but are not limited to, the compounds listed below, while any known cationically-polymerizable compound may be used with no problem. For the purpose of controlling the reaction rate, the physical properties of the ink, the physical properties of the cured film, or the like, one or more cationically-polymerizable compounds may be used singly or in combination.

Any known cationically-polymerizable compound may be used, and examples thereof include not only styrene derivatives and vinyl ethers but also oxiranes, oxetanes, tetrahydrofurans, lactams, and lactones. In particular, oxiranes, oxetanes, vinyl ethers, or styrene derivatives are preferably used. Oxiranes and oxetanes are particularly preferred.

Besides the compound according to the present invention, one or more oxirane ring-containing compounds (oxirane compounds, namely epoxy compounds) and/or one or more oxetane ring-containing compounds (oxetane compounds) may be used singly or in combination. In terms of improving the curing rate and the degree of curing, at least one oxetane compound and at least one oxirane compound are preferably used in combination. In this case, the oxirane compound and the oxetane compound are preferably used in a ratio of 10:90 to 70:30. Within this range, an ink composition having a good balance between curing property and curing rate can be obtained.

In terms of stably ejecting ink, the aforementioned another cationically-polymerizable compound for use in the present invention preferably has low viscosity and may include any monofunctional cationically-polymerizable compound. An oxirane, oxetane, or vinyl ether is preferably used as the monofunctional cationically-polymerizable compound, and in particular, one or both of an oxirane and an oxetane is preferably used alone or in combination. If the monofunctional cationically-polymerizable compound is too much, the curing property can be reduced. If it is too little, the viscosity of the ink can be increased. The monofunctional cationically-polymerizable compound is preferably used in an amount of 3% by mass to 50% by mass, most preferably of 5% by mass to 40% by mass, together with the compound according to the present invention, based on the total amount of the ink composition.

[Oxirane Compound]

Examples of the oxirane compounds include aromatic epoxides, alicyclic epoxides, and the like.

Examples of the aromatic epoxides include di- or polyglycidyl ethers prepared by allowing a polyhydric phenol having at least one aromatic ring or the alkyleneoxide adduct thereof to react with epichlorohydrin; and examples thereof include di- or poly-glycidyl ethers of bisphenol A or the alkyleneoxide adduct thereof, di- or poly-glycidyl ethers of a hydrogenated bisphenol A or the alkyleneoxide adduct thereof, novolak epoxy resins, and the like. Examples of the alkyleneoxide include ethyleneoxide, propyleneoxide, and the like.

Examples of the alicyclic epoxide include compounds including cyclohexeneoxide or cyclopenteneoxide obtained by epoxidating a compound having at least one cycloalkane ring such as a cyclohexene or cyclopentene ring with a proper oxidizer such as hydrogen peroxide, or peroxy acid.

Examples of the aliphatic epoxide include diglycidyl ether or polyglycidyl ether of aliphatic polyalcohol or its alkyleneoxide adduct. Typical examples thereof include diglycidyl ether of alkyleneglycol such as diglycidyl ether of ethyleneglycol, diglycidyl ether of propyleneglycol, diglycidyl ether of 1,6-hexanediol; polyglycidyl ether of polyalcohol such as diglycidyl ether or triglycidyl ether of glycerin or its alkyleneoxide adduct; and diglycidyl ether of polyalkyleneglycol such as diglycicyl ether of polyethyleneglycol or its alkyleneoxide adduct, diglycidyl ether of polypropyleneglycol or its alkyleneoxide adduct. Here, examples of the alkyleneoxide include ethyleneoxide and propyleneoxide.

Among the oxirane compounds, from the viewpoint of rapid curability, preferred are the aromatic epoxide and the alicyclic epoxide, and particularly preferred is the alicyclic epoxide.

Examples of the monofunctional epoxide for use in the present invention include phenyl glycidyl ether, p-tert-butylphenyl glycidyl ether, butyl glycidyl ether, 2-ethylhexyl glycidyl ether, allyl glycidyl ether, 1,2-butyleneoxide, 1,3-butadienemonooxide, 1,2-epoxydodecane, epichlorohydrin, 1,2-epoxydecane, styreneoxide, cyclohexeneoxide, 3-methacryloyloxymethylcyclohexeneoxide, 3-acryloyloxymethylcyclohexeneoxide, 3-vinylcylcohexeneoxide, and the like.

Examples of multifunctional epoxy compounds include bisphenol A diglycidyl ether, bisphenol F diglycidyl ether, bisphenol S diglycidyl ether, brominated bisphenol A diglycidyl ether, brominated bisphenol F diglycidyl ether, brominated bisphenol S diglycidyl ether, epoxy novolak resin, hydrogenated bisphenol A diglycidyl ether, hydrogenated bisphenol F diglycidyl ether, hydrogenated bisphenol S diglycidyl ether, 3,4-epoxycyclohexyl methyl-3',4'-epoxycyclohexane carboxylate, 2-(3,4-epoxycyclohexyl-5,5-spiro-3,4-epoxy)cyclohexane-meta-dioxane, bis(3,4-epoxycyclohexylmethyl) adipate, vinylcyclohexene oxide, 4-vinylepoxycyclohexane, bis(3,4-epoxy-6-methylcyclohexylmethyl)adipate, 3,4-epoxy-6-methylcyclohexyl-3',4'-epoxy-6'-methylcyclohexane carboxylate, methylenebis(3,4-epoxycyclohexane), dicylopentadiene diepoxide, di(3,4-epoxycyclohexylmethyl)ether of ethyleneglycol; ethylenebis (3,4-epoxycyclohexane carboxylate), dioctyl epoxyhexahydrophthalate, di-2-ethylhexyl epoxyhexahydrophthalate, 1,4-butanediol diglycidyl ether, 1,6-hexanediol diglycidyl ether, glycerin triglycidyl ether, trimethylolpropane triglycidyl ether, polyethylene glycol diglycidyl ether, polypropylene glycol diglycidyl ethers, 1,1,3-tetradecadiene dioxide, limonene dioxide, 1,2,7,8-diepoxy octane, and 1,2, 5,6-diepoxy cyclooctane.

[Oxetane Compound]

The "oxetane compound that may be used in combination in the ink composition of the present invention" refers to a compound having an oxetane ring, and any compound may be arbitrarily selected and used from known oxetane compounds such as those disclosed in JP-A-2001-220526, JP-A-2001-310937, and JP-A-2003-341217.

The oxetane ring-containing compound for use in the ink composition according to the present invention is preferably a compound having 1 to 4 oxetane rings in the structure, and among them, use of a compound having 1 or 2 oxetane rings is preferable from the viewpoints of the viscosity and tackiness of the ink composition. Use of such a compound makes it easier to keep the viscosity of the ink composition in the range favorable for handling and make the cured ink more adhesive to the recording medium.

Examples of the compound having one or two oxetane rings in its molecule include compounds represented by the following formulae (1) to (3).

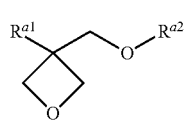

(1)

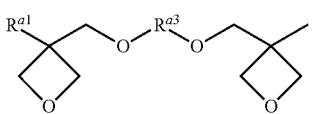

(2)

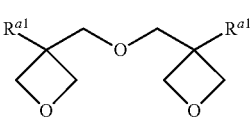

(3)

$R^{a1}$ represents a hydrogen atom, an alkyl group having 1 to 6 carbon atoms, a fluoroalkyl group having 1 to 6 carbon atoms, an allyl group, an aryl group, a furyl group, or a thienyl group. If the molecule has two $R^{a1}$ groups, they may be the same or different.

Examples of the alkyl group include methyl, ethyl, propyl, and butyl, and examples of the fluoroalkyl group include these alkyl groups in which any hydrogen atom or atoms are replaced by a fluorine atom or atoms.

$R^{2a}$ represents an alkyl group having 1 to 6 carbon atoms, an alkenyl group having 2 to 6 carbon atoms, a group having an aromatic ring, an alkylcarbonyl group having 2 to 6 carbon atoms, an alkoxycarbonyl group having 2 to 6 carbon atoms, or an N-alkylcarbamonyl group having 2 to 6 carbon atoms. Examples of the alkyl group include methyl, ethyl, propyl, and butyl. Examples of the alkenyl group include 1-propenyl, 2-propenyl, 2-methyl-1-propenyl, 2-methyl-2-propenyl, 1-butenyl, 2-butenyl, and 3-butenyl. Examples of the group having an aromatic ring include phenyl, benzyl, fluorobenzyl, methoxybenzyl, and phenoxyethyl. Examples of the alkylcarbonyl group include ethylcarbonyl, propylcarbonyl, and butylcarbonyl. Examples of the alkoxycarbonyl group include ethoxycarbonyl, propoxycarbonyl, and butyloxycarbonyl. Examples of the N-alkylcarbamoyl group include ethylcarbamoyl, propylcarbamoyl, butylcarbamoyl, and pentylcarbamoyl.

$R^{a3}$ represents a linear or branched alkylene group, a linear or branched poly(alkyleneoxy) group, a linear or branched unsaturated hydrocarbon group, a carbonyl group or a carbonyl-containing alkylene group, a carboxyl-containing alkylene group, a carbamoyl-containing alkylene group, or the group shown below. Examples of the alkylene group include ethylene, propylene, and butylene groups, and examples of the poly(alkyleneoxy) group include poly(ethyleneoxy) and poly(propyleneoxy) groups. Examples of the unsaturated hydrocarbon group include propenylene, methylpropenylene, and butenylene groups.

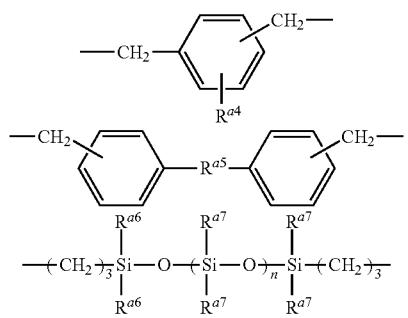

When $R^{a3}$ is the above multivalent group, $R^{a4}$ represents a hydrogen atom, an alkyl group having 1 to 4 carbon atoms, an alkoxy group having 1 to 4 carbon atoms, a halogen atom, a nitro group, a cyano group, a mercapto group, a lower alkylcarboxyl group, a carboxyl group, or a carbamoyl group.

$R^{a5}$ represents an oxygen atom, a sulfur atom, a methylene group, NH, SO, $SO_2$, $C(CF_3)_2$, or $C(CH_3)_2$.

$R^{a6}$ represents an alkyl group having 1 to 4 carbon atoms, or aryl group, and n is an integer of 0 to 2,000.

$R^{a7}$ represents an alkyl group having 1 to 4 carbon atoms, an aryl group, or a monovalent group having the structure shown below. In the following formula, $R^{a8}$ represents an alkyl group having 1 to 4 carbon atoms, and an aryl group; and m represents an integer of 0 to 100.

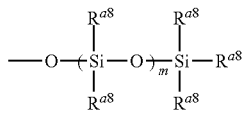

Examples of the compound having three or four oxetane rings include compounds represented by the following formula (4).

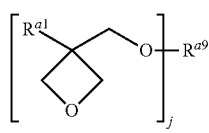

In formula (4), $R^{a1}$ has the same meaning as defined in formula (1). $R^{a9}$ is a multivalent linking group and, for example, may be a branched alkylene group having 1 to 12 carbon atoms, such as the group represented by formula A, B or C below; a branched poly(alkyleneoxy) group such as the group represented by formula D below; or a branched polysiloxy group such as the group represented by formula E below. In formula (4), j is 3 or 4.

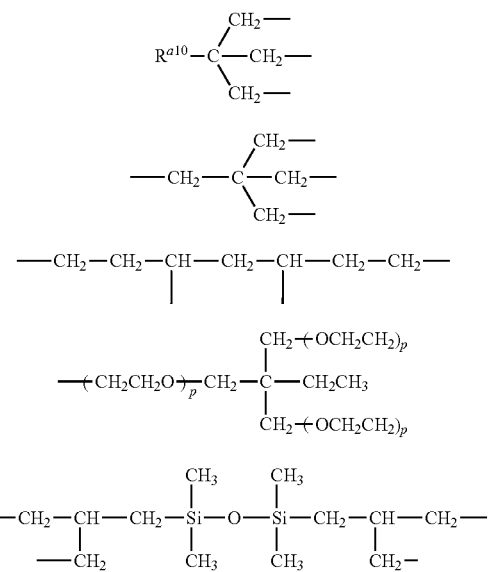

In formula A above, $R^{a10}$ is a methyl, ethyl, or propyl group. In formula D above, p is an integer of 1 to 10.

Another mode of the oxetane compound that may be preferably used in combination according to the present invention is a compound that has an oxetane ring in its side chain and is represented by formula (5):

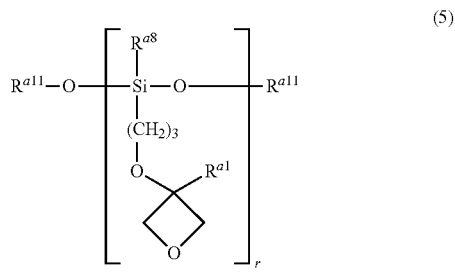

In formula (5), $R^{a1}$ and $R^{a8}$ each have the same meaning as defined in the above formula. $R^{a11}$ is a trialkylsilyl group or an alkyl group having 1 to 12 carbon atoms, such as methyl, ethyl, propyl, and butyl. r is 1 to 4.

The oxetane compound that may be used in combination with the compound for use in the present invention, may be monofunctional or multifunctional.

Examples of monofunctional oxetanes usable in the present invention include 3-ethyl-3-hydroxymethyl oxetane, 3-(meth)allyloxymethyl-3-ethyl oxetane, (3-ethyl-3-oxetanylmethoxy)methyl benzene, 4-fluoro-[1-(3-ethyl-3-oxetanylmethoxy)methyl]benzene, 4-methoxy-[1-(3-ethyl-3-oxetanylmethoxy)methyl]benzene, [1-(3-ethyl-3-oxetanylmethoxy)ethyl]phenyl ether, isobutoxymethyl(3-ethyl-3-oxetanylmethyl)ether, isobornyloxyethyl(3-ethyl-3-oxetanylmethyl)ether, isobornyl(3-ethyl-3-oxetanylmethyl) ether, 2-ethylhexyl(3-ethyl-3-oxetanylmethyl)ether, ethyldiethylene glycol(3-ethyl-3-oxetanylmethyl)ether, dicyclopentadiene (3-ethyl-3-oxetanylmethyl)ether, dicyclopentenyloxyethyl (3-ethyl-3-oxetanylmethyl)ether, dicyclopentenyl (3-ethyl-3-oxetanylmethyl)ether, tetrahydrofurfuryl (3-ethyl-3-oxetanylmethyl)ether, tetrabromophenyl (3-ethyl-3-oxetanylmethyl)ether, 2-tetrabromophenoxyethyl (3-ethyl-3-oxetanylmethyl)ether, tribromophenyl (3-ethyl-3-oxetanylmethyl)ether, 2-tribromophenoxyethyl (3-ethyl-3-oxetanylmethyl)ether, 2-hydroxyethyl (3-ethyl-3-oxetanylmethyl)ether, 2-hydroxypropyl (3-ethyl-3-oxetanylmethyl) ether, butoxyethyl (3-ethyl-3-oxetanylmethyl)ether, pentachlorophenyl (3-ethyl-3-oxetanylmethyl)ether, pentabromophenyl (3-ethyl-3-oxetanylmethyl)ether, and bornyl (3-ethyl-3-oxetanylmethyl)ether.

Examples of multifunctional oxetanes include 3,7-bis(3-oxetanyl)-5-oxa-nonane, 3,3'-(1,3-(2-methylenyl)propanediyl-bis(oxymethylene))bis-(3-ethyloxetane), 1,4-bis [(3-ethyl-3-oxetanylmethoxy)methyl]benzene, 1,2-bis[(3-ethyl-3-oxetanylmethoxy)methyl]ethane, 1,3-bis[(3-ethyl-3-oxetanylmethoxy)methyl]propane, ethylene glycol bis(3-ethyl-3-oxetanylmethyl)ether, dicyclopentenyl bis(3-ethyl-3-oxetanylmethyl)ether, triethylene glycol bis(3-ethyl-3-oxetanylmethyl)ether, tetraethylene glycol bis(3-ethyl-3-oxetanylmethyl)ether, tricyclodecanediyldimethylene(3-ethyl-3-oxetanylmethyl)ether, trimethylolpropane tris(3-ethyl-3-oxetanylmethyl)ether, 1,4-bis(3-ethyl-3-oxetanylmethoxy)butane, 1,6-bis(3-ethyl-3-oxetanylmethoxy)hexane, pentaerythritol tris(3-ethyl-3-oxetanylmethyl)ether, pentaerythritol tetrakis(3-ethyl-3-oxetanylmethyl)ether, polyethylene glycol bis(3-ethyl-3-oxetanylmethyl)ether, dipentaerythritol hexakis(3-ethyl-3-oxetanylmethyl)ether, dipentaerythritol pentakis(3-ethyl-3- oxetanylmethyl)ether, dipentaerythritol tetrakis(3-ethyl-3-oxetanylmethyl)ether, caprolactone-modified dipentaerythritol hexakis(3-ethyl-3-oxetanylmethyl)ether, caprolactone-modified dipentaerythritol pentakis(3-ethyl-3-oxetanylmethyl)ether, ditrimethylolpropane tetrakis(3-ethyl-3-oxetanylmethyl)ether, EO-modified bisphenol A bis(3-ethyl-3-oxetanylmethyl)ether, PO-modified bisphenol A bis(3-ethyl-3-oxetanylmethyl)ether, EO-modified hydrogenated bisphenol A bis(3-ethyl-3-oxetanylmethyl) ether, PO-modified hydrogenated bisphenol A bis(3-ethyl-3-oxetanylmethyl)ether, and EO-modified bisphenol F (3-ethyl-3-oxetanylmethyl)ether.

[Vinyl Ether]

According to the present invention, a vinyl ether group-containing compound may also be added in order to provide a certain degree of curing. In this case, the ink composition may contain 1% by mass to 20% by mass of the vinyl ether group-containing compound, in view of the physical properties of the cured product surface or the control of the solubility of the ink composition.

Examples of monofunctional vinyl ethers usable in the present invention include methyl vinyl ether, ethyl vinyl ether, propyl vinyl ether, n-butyl vinyl ether, t-butyl vinyl ether, 2-ethylhexyl vinyl ether, n-nonyl vinyl ether, lauryl vinyl ether, cyclohexyl vinyl ether, cyclohexyl methyl vinyl ether, 4-methylcyclohexylmethyl vinyl ether, benzyl vinyl ether, dicyclopentenyl vinyl ether, 2-dicyclopentenoxy ethyl vinyl ether, methoxyethyl vinyl ether, ethoxyethyl vinyl ether, butoxyethyl vinyl ether, methoxyethoxyethyl vinyl ether, ethoxyethoxyethyl vinyl ether, methoxy polyethylene glycol vinyl ether, tetrahydrofurfuryl vinyl ether, 2-hydroxyethyl vinyl ether, 2-hydroxypropyl vinyl ether, 4-hydroxybutyl vinyl ether, 4-hydroxymethylcyclohexylmethyl vinyl ether, diethylene glycol monovinyl ether, polyethylene glycol vinyl ether, chloroethyl vinyl ether, chlorobutyl vinyl ether, chloroethoxyethyl vinyl ether, phenylethyl vinyl ether, and phenoxy polyethylene glycol vinyl ether.

Examples of multifunctional vinyl ethers include: divinyl ethers such as ethylene glycol divinyl ether, diethylene glycol divinyl ether, polyethylene glycol divinyl ether, propylene glycol divinyl ether, butylene glycol divinyl ether, hexanediol divinyl ether, bisphenol A alkylene oxide divinyl ether, and bisphenol F alkylene oxide divinyl ether; and multifunctional vinyl ethers such as trimethylolethane trivinyl ether, trimethylolpropane trivinyl ether, ditrimethylolpropane tetravinyl ether, glycerin trivinyl ether, pentaerythritol tetravinyl ether, dipentaerythritol pentavinyl ether, dipentaerythritol hexavinyl ether, ethylene oxide-added trimethylolpropane trivinyl ether, propylene oxide-added trimethylolpropane trivinyl ether, ethylene oxide-added ditrimethylolpropane tetravinyl ether, propylene oxide-added ditrimethylolpropane tetravinyl ether, ethylene oxide-added pentaerythritol tetravinyl ether, propylene oxide-added pentaerythritol tetravinyl ether, ethylene oxide-added dipentaerythritol hexavinyl ether, and propylene oxide-added dipentaerythritol hexavinyl ether.

[Styrene Derivatives]

According to the present invention, any styrene derivative may also be added. In this case, while known compounds may be used as the styrene derivative, it is preferred to use a styrene derivative having an electron-donating functional group as a substituent at least one of the p- and o-positions of the aromatic ring, in terms of increasing the electron density on the vinyl group. As used herein, the term "electron-donating functional group" refers to a functional group having a negative substituent constant σ according to the Hammett rule. Examples of such a functional group include amino, hydroxyl, alkoxy, and alkyl groups. In particular, alkoxy, alkyl, and dimethylamino groups are preferably used, because they hardly react with active ends during polymerization.

Examples of the monofunctional styrene compound include styrene; 2-alkylstyrenes and 4-alkylstyrenes, such as 2-methylstyrene, 4-methylstyrene, 2,6-methylstyrene, 2-ethylstyrene, 4-ethylstyrene, 2-ethylstyrene, 4-n-butylstyrene, 2-n-butylstyrene, 4-tert-butylstyrene, 2-tert-butylstyrene, 4-butenylstyrene, and 4-octenylstyrene; 2-alkoxystyrenes or 4-alkoxystyrenes, such as 4-methoxystyrene, 2-methoxystyrene, and 4-tert-butylstyrene; and 4-acetoxystyrene, 4-dimethylaminostyrene, 4-dimethylaminomethylstyrene, 4-glycidylmethylstyrene, 4-hydroxystyrene, 2,4-dialkylstyrene, 2,4,6-trialkylstyrene, 2,4-dialkoxystyrene, and 2,4,6-trialkoxystyrene.

Examples of the multifunctional styrene include divinylbenzene, bis(4-vinylphenyl)methane, bis(4-vinylphenyl)ethane, bis(4-vinylphenyl)butane, bis(4-vinylphenyl)hexane, bis(4-vinylphenyl)heptane, bis(4-vinylphenyl)octane, bis(4-vinylphenoxy)hexane, bis(4-vinylbenzyl)diethylene glycol, ethylene glycol bis(4-vinylphenyl)ether, propylene glycol bis(4-vinylphenyl)ether, 1,6-hexanediol bis(4-vinylphenyl)ether, 1,8-octanediol bis(4-vinylphenyl)ether, oligoethylene glycol bis(4-vinylphenyl)ether, polyethylene glycol (4-vinylphenyl ether), oligopropylene glycol bis(4-vinylphenyl)ether, polypropylene glycol bis(4-vinylphenyl)ether, and glycerin tris(4-vinylphenyl)ether.

In view of curing property, the ink composition of the present invention preferably includes at least one polymerization initiator and at least one photosensitizer.

[Polymerization Initiator]

A photocationic polymerization initiator is preferably used as the polymerization initiator in the present invention. The photocationic polymerization initiator is a compound that generates acid and initiates cationic polymerization by irradiation of an activated or radiation ray, and any one of known compounds and the mixtures thereof properly selected may be used.

The following photocationic polymerization initiators may be used as a single initiator or as a mixture of two or more initiators. The content of the photocationic polymerization initiator in the ink composition is preferably in the range of 0.1 to 20% by mass and more preferably 0.5 to 10% by mass. A too-small photocationic polymerization initiator content may lead to reduction in the amount of acid generated and deterioration in curing property, while a too-large photocationic polymerization initiator content may lead to problems such as brittleness of the cured product and generation of acid by the residual initiator.

Examples of the photocationic polymerization initiators according to the present invention include diazonium salts, phosphonium salts, sulfonium salts, iodonium salts, imide sulfonates, oxime sulfonates, diazo disulfones, disulfones, and o-nitrobenzyl sulfonates.

These photocationic polymerization initiators or the compounds having a group or compound equivalent in action introduced on the polymer main or side chain, for example, the compounds described in U.S. Pat. No. 3,849,137, Germany Patent 3914407, JP-A-63-26653, JP-A-55-164824, JP-A-62-69263, JP-A-63-146038, JP-A-63-163452, JP-A-62-153853, and JP-A-63-146029, and others may be used.

The compounds that generate acid by irradiation of light described in U.S. Pat. No. 3,779,778, EP Patent No. 126,712, and others may also be used.

For example, a compound represented by formula (b1), (b2) or (b3) below may be preferably used as the photocationic polymerization initiator in the present invention.

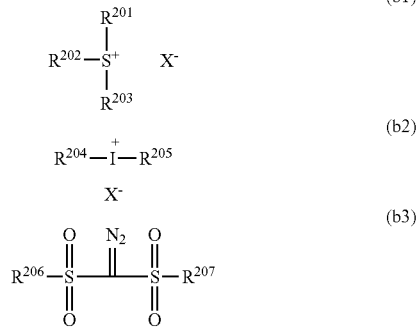

In formula (b1), $R^{201}$, $R^{202}$, and $R^{203}$ each independently represent an organic group.

$X^-$ represents a non-nucleophilic anion, which is preferably sulfonate anion, carboxylate anion, bis(alkylsulfonyl)amide anion, tris(alkylsulfonyl)methide anion, $BF_4^-$, $PF_6^-$, $SbF_6^-$, or the group shown below, and more preferably a carbon-atom-containing organic anion.

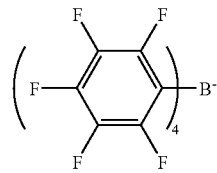

Preferable examples of the organic anion include organic anions represented by the following formulas.

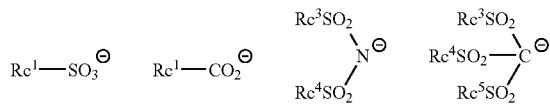

$Rc^1$ represents an organic group.

Examples of the organic group $Rc^1$ include organic groups of 1 to 30 carbon atoms and preferably include alkyl, cycloalkyl, aryl, and a group having two or more of the above groups linked by a single bond or a linking group such as —O—, —CO$_2$—, —S—, —SO$_3$—, —SO$_2$N(Rd$^1$)—.

$Rd^1$ represents a hydrogen atom or an alkyl group. $Rc^3$, $Rc^4$, and $Rc^5$ each independently represent an organic group. Examples of the organic group $Rc^3$, $Rc^4$ or $Rc^5$ preferably include the same as those of the organic group $Rc^1$, and most preferably a perfluoroalkyl group having 1 to 4 carbon atoms. $Rc^3$ and $Rc^4$ may bond to each other to form a ring. The group formed by bonding $Rc^3$ and $Rc^4$ may be an alkylene or arylene group, preferably a perfluoroalkylene group having 2 to 4 carbon atoms.

The organic groups $Rc^1$ and $Rc^3$ to $Rc^5$ are each most preferably an alkyl group substituted with a fluorine atom or a fluoroalkyl group at its 1-position or a phenyl group substituted with a fluorine atom or a fluoroalkyl group. The presence of the fluorine atom or the fluoroalkyl group can raise the acidity of the acid produced by photoirradiation and increase the sensitivity.

The number of carbon atoms of the organic group $R^{201}$, $R^{202}$ or $R^{203}$ is preferably from 1 to 30, more preferably from 1 to 20.

Two of the $R^{201}$ to $R^{203}$ groups may bond to each other to form a ring structure, and the ring structure may contain an oxygen atom, a sulfur atom, an ester bond, an amide bond, or a carbonyl group. The two of the $R^{201}$ to $R^{203}$ groups may bond to each other to form a group, and the group may be an alkylene group (e.g. a butylene or pentylene group).

Examples of the organic groups $R^{201}$, $R^{202}$ and $R^{203}$ include the corresponding groups in Compounds (b1-1), (b1-2), and (b1-3) described later.

A compound having two or more structures of formula (b1) may also be used. For example, such a compound may have a structure in which at least one of $R^{201}$ to $R^{203}$ of a compound represented by formula (b1) is directly bonded to or bonded through a linking group to at least one of $R^{201}$ to $R^{203}$ of another compound represented by formula (b1).

Preferred examples of the (b1) component also include Compounds (b1-1), (b1-2), and (b1-3) described below.

Compound (b1-1) is an aryl sulfonium compound in which at least one of $R^{201}$ to $R^{203}$ of formula (b1) is an aryl group, namely a compound having an aryl sulfonium cation.

In the aryl sulfonium compound, all of $R^{201}$ to $R^{203}$ may each be an aryl group, or some of $R^{201}$ to $R^{203}$ may be an aryl group(s), while the remainder may be an alkyl or cycloalkyl group(s).

Examples of the aryl sulfonium compound include triaryl sulfonium compounds, diaryl alkyl sulfonium compounds, aryl dialkyl sulfonium compounds, diaryl cycloalkyl sulfonium compounds, and aryl dicycloalkyl sulfonium compounds.

The aryl group of the aryl sulfonium compound is preferably an aryl group such as phenyl and naphthyl or a heteroaryl group such as an indole or pyrrole residue, more preferably a phenyl group or an indole residue. When the aryl sulfonium compound has two or more aryl groups, they may be the same or different.

The alkyl group optionally contained in the aryl sulfonium compound is preferably a linear or branched alkyl group having 1 to 15 carbon atoms, such as methyl, ethyl, propyl, n-butyl, sec-butyl, and tert-butyl.

The cycloalkyl group optionally contained in the aryl sulfonium compound is preferably a cycloalkyl group having 3 to 15 carbon atoms, such as cyclopropyl, cyclobutyl, and cyclohexyl.

The aryl, alkyl or cycloalkyl group of $R^{201}$ to $R^{203}$ may have a substituent of an alkyl group (e.g. an alkyl group having 1 to 15 carbon atoms), a cycloalkyl group (e.g. a cycloalkyl group having 3 to 15 carbon atoms), an aryl group (e.g. an aryl group having 6 to 14 carbon atoms), an alkoxy group (e.g. an alkoxy group having 1 to 15 carbon atoms), a halogen atom, a hydroxyl group, or a phenylthio group. The substituent is preferably a linear or branched alkyl group having 1 to 12 carbon atoms, a cycloalkyl group having 3 to 12 carbon atoms, or a linear, branched or cyclic alkoxy group having 1 to 12 carbon atoms, most preferably an alkyl group having 1 to 4 carbon atoms or an alkoxy group having 1 to 4 carbon atoms. The substituent may be present in any one or all of the three groups $R^{201}$ to $R^{203}$. When $R^{201}$ to $R^{203}$ are each aryl, the substituent is preferably present at the p-position of the aryl group.

Next, Compound (b1-2) will be explained.

Compound (b1-2) is a compound in which $R^{201}$ to $R^{203}$ of formula (b1) each independently represent an aromatic ring-free organic group, wherein the aromatic ring also includes a heteroatom-containing aromatic ring.

The aromatic ring-free organic groups represented by $R^{201}$ to $R^{203}$ are preferably of 1 to 30 carbon atoms, more preferably of 1 to 20 carbon atoms.

Preferably, $R^{201}$ to $R^{203}$ are each independently alkyl, cycloalkyl, allyl, or vinyl, more preferably a linear, branched or cyclic 2-oxoalkyl or alkoxycarbonylmethyl group, particularly preferably a linear or branched 2-oxoalkyl group.

The alkyl group for $R^{201}$ to $R^{203}$ may be linear or branched and is preferably a linear or branched alkyl group having 1 to 10 carbon atoms (e.g. methyl, ethyl, propyl, butyl, and pentyl), more preferably a linear or branched 2-oxoalkyl or alkoxycarbonylmethyl group.

The cycloalkyl group for $R^{201}$ to $R^{203}$ is preferably a cycloalkyl group having 3 to 10 carbon atoms (e.g. cyclopentyl, cyclohexyl, and norbornyl), more preferably a cyclic 2-oxoalkyl group.

The linear, branched or cyclic 2-oxoalkyl group for $R^{201}$ to $R^{203}$ is preferably the above alkyl or cycloalkyl group having >C=O at the 2-position.

The alkoxy group of the alkoxycarbonylmethyl group for $R^{201}$ to $R^{203}$ is preferably an alkoxy group having 1 to 5 carbon atoms (e.g. methoxy, ethoxy, propoxy, butoxy, and pentoxy).

$R^{201}$ to $R^{203}$ may be further substituted with a halogen atom, an alkoxy group (e.g. an alkoxy group having 1 to 5 carbon atoms), a hydroxyl group, a cyano group, or a nitro group.

Compound (b1-3) is a compound represented by formula (b1-3) below and has a phenacylsulfonium salt structure.

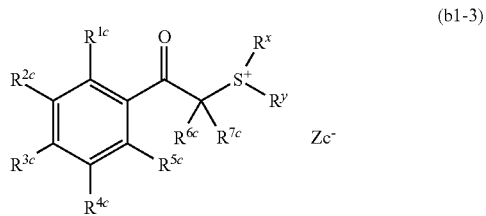

(b1-3)

In formula (b1-3), $R^{1c}$ to $R^{5c}$ each independently represent a hydrogen atom, an alkyl group, a cycloalkyl group, an alkoxy group, or a halogen atom; $R^{6c}$ and $R^{7c}$ each independently represent a hydrogen atom, an alkyl group or a cycloalkyl group; $R^x$ and $R^y$ each independently represent an alkyl group, a cycloalkyl group, an allyl group, or a vinyl group; any two or more of $R^{1c}$ to $R^{5c}$, $R^{6c}$ and $R^{7c}$, or $R^x$ and $R^y$ may bond to each other to form a ring structure; and $Zc^-$ represents a non-nucleophilic anion, examples of which may include the same as those for the non-nucleophilic anion $X^-$ in formula (b1).

The alkyl group for $R^{1c}$ to $R^{7c}$ may be linear or branched and is preferably a linear or branched alkyl group having 1 to 20 carbon atoms, more preferably a linear or branched alkyl group having 1 to 12 carbon atoms (e.g. methyl, ethyl, linear or branched propyl, linear or branched butyl, and linear or branched pentyl).

The cycloalkyl group for $R^{1c}$ to $R^{7c}$ is preferably a cycloalkyl group having 3 to 8 carbon atoms (e.g. cyclopentyl, and cyclohexyl).

The alkoxy group for $R^{1c}$ to $R^{5c}$ may be linear, branched or cyclic and is typically an alkoxy group having 1 to 10 carbon atoms, preferably a linear or branched alkoxy group having 1 to 5 carbon atoms (e.g. methoxy, ethoxy, linear or branched propoxy, linear or branched butoxy, and linear or branched pentoxy) or a cyclic alkoxy group having 3 to 8 carbon atoms (e.g. cyclopentyloxy and cyclohexyloxy).

The group formed by bonding two or more of $R^{1c}$ to $R^{5c}$, bonding $R^{6c}$ and $R^{7c}$ or bonding $R^x$ and $R^y$ may be a butylene or pentylene group. This ring structure may contain an oxygen atom, a sulfur atom, an ester bond, or an amide bond.

Preferably, any of $R^{1c}$ to $R^{5c}$ is a linear or branched alkyl group, a cycloalkyl group, or a linear, branched or cyclic alkoxy group, and more preferably the total number of carbon atoms of $R^{1c}$ to $R^{5c}$ is from 2 to 15. This feature can increase the solubility in solvents and inhibit the generation of particles during storage.

Examples of the alkyl or cycloalkyl group for $R^x$ and $R^y$ may be the same as those of the alkyl or cycloalkyl group for $R^{1c}$ to $R^{7c}$.

$R^x$ and $R^y$ are each preferably a 2-oxoalkyl group or an alkoxycarbonylmethyl group.

An example of the 2-oxoalkyl group is a group which has >C=O at the 2-position of the alkyl or cycloalkyl group for $R^{1c}$ to $R^{5c}$.

Examples of the alkoxy group of the alkoxycarbonylmethyl group may be the same as those of the alkoxy group for $R^{1c}$ to $R^{5c}$.

$R^x$ and $R^y$ are each preferably an alkyl or cycloalkyl group of 4 or more carbon atoms, more preferably of 6 or more carbon atoms, still more preferably of 8 or more carbon atoms.

In formulas (b2) and (b3), $R^{204}$ to $R^{207}$ each independently represent an aryl group, an alkyl group, or a cycloalkyl group; $X^-$ represents a non-nucleophilic anion, examples of which may include the same as those for the non-nucleophilic anion $X^-$ in formula (b1).

The aryl group for $R^{204}$ to $R^{207}$ is preferably a phenyl group or a naphthyl group, and more preferably a phenyl group.

The alkyl group for $R^{204}$ to $R^{207}$ may be linear or branched and is preferably a linear or branched alkyl group having 1 to 10 carbon atoms (e.g. methyl, ethyl, propyl, butyl, and pentyl). The cycloalkyl group for $R^{204}$ to $R^{207}$ is preferably a cycloalkyl group having 3 to 10 carbon atoms (e.g. cyclopentyl, cyclohexyl, and norbornyl).

Examples of the substituent optionally contained in $R^{204}$ to $R^{207}$ include an alkyl group (e.g. an alkyl group having 1 to 15 carbon atoms), a cycloalkyl group (e.g. a cycloalkyl group having 3 to 15 carbon atoms), an aryl group (e.g. an aryl group having 6 to 15 carbon atoms), an alkoxy group (e.g. an alkoxy group having 1 to 15 carbon atoms), a halogen atom, a hydroxyl group, and a phenylthio group.

A compound represented by formula (b4), (b5), or (b6) below may also be used as the photocationic polymerization initiator.

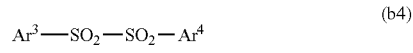

(b4)

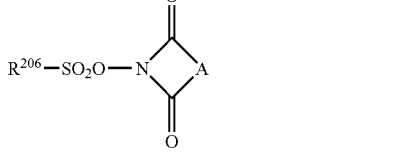

(b5)

-continued

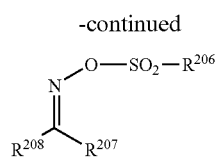

In formulae (b4) to (b6), $Ar^3$ and $Ar^4$ each independently represent an aryl group; $R^{206}$, $R^{207}$, and $R^{208}$ each independently represent an alkyl group, a cycloalkyl group or an aryl group; and A represents an alkylene group, an alkenylene group or an arylene group.

Among the above photocationic polymerization initiators, the compounds represented by formulae (b1) to (b3) are preferred.

Particularly preferred examples of the photocationic polymerization initiator that may be used in the present invention include, but are not limited to, the compounds shown below.

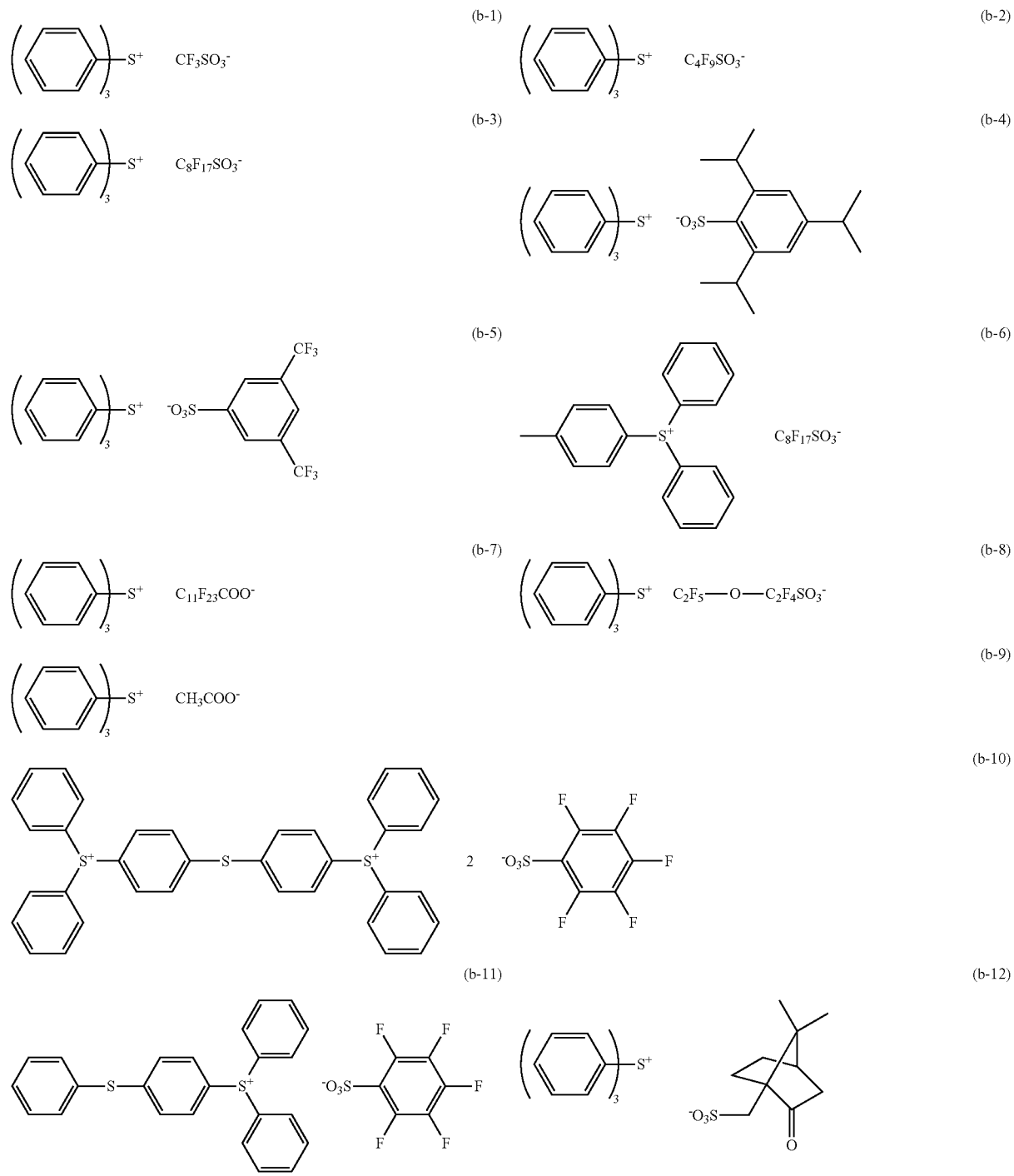

-continued

-continued
(b-29)
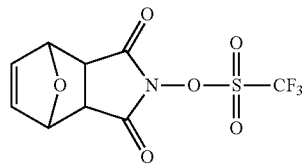
(b-30)
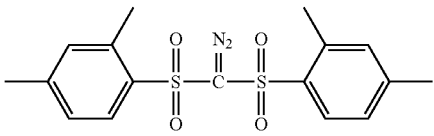
(b-31)
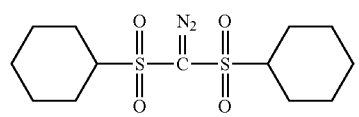
(b-32)
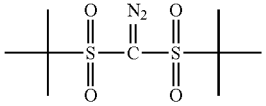
(b-33)
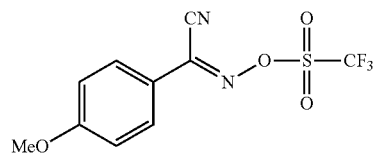
(b-34)
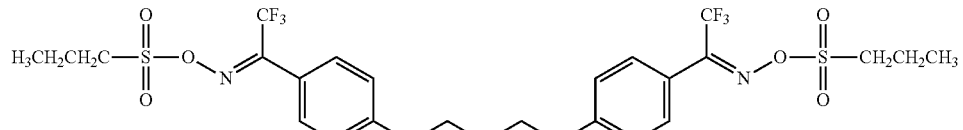
(b-35)
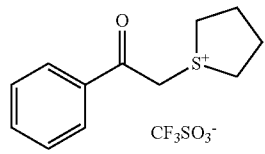
(b-36)
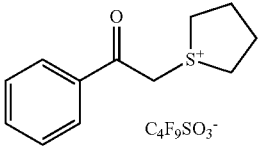
(b-37)
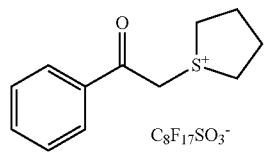
(b-38)
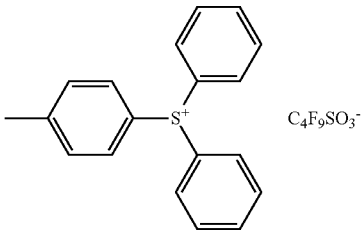
(b-39)
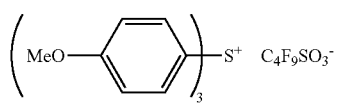
(b-40)
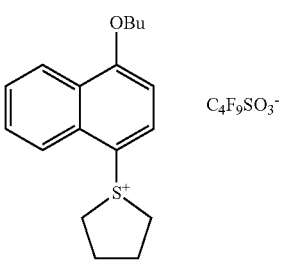
(b-41)
(b-42)
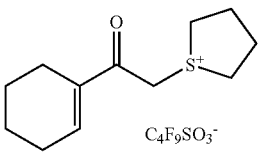

-continued
(b-43) 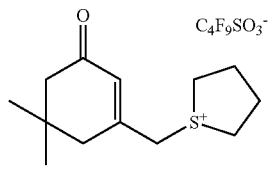
(b-44) 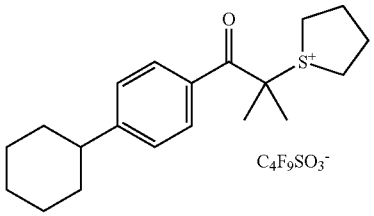
(b-45) 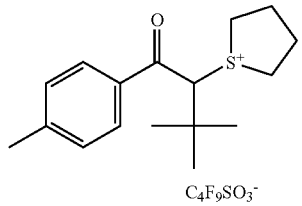
(b-46) 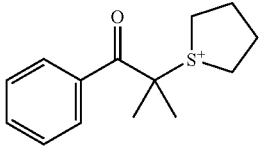
(b-47) 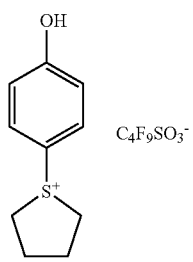
(b-48) 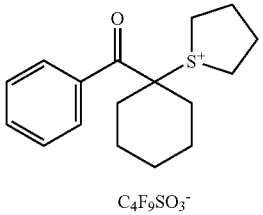
(b-49) 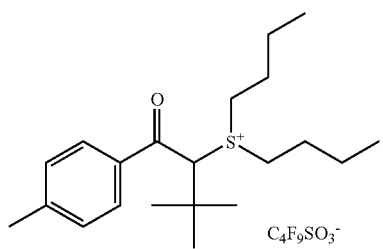
(b-50) 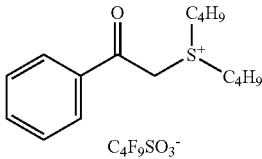
(b-51) 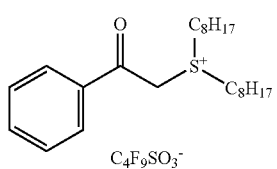
(b-52) 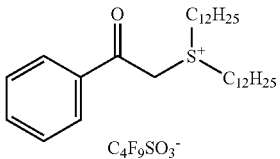
(b-53) 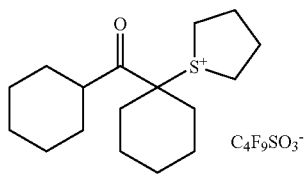
(b-54) 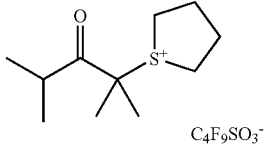
(b-55) 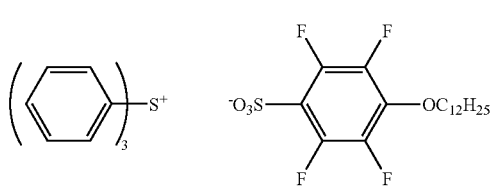
(b-56) 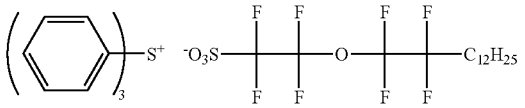

-continued

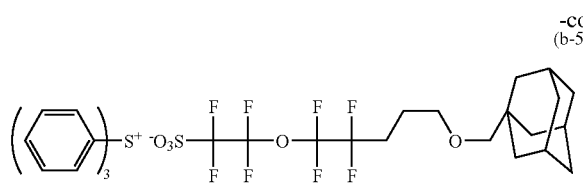
(b-57)

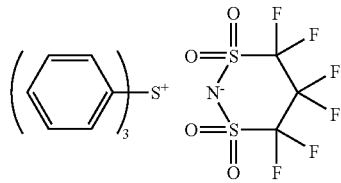
(b-58)

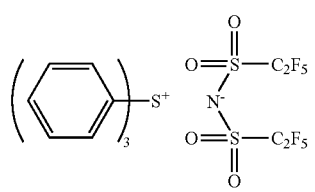
(b-59)

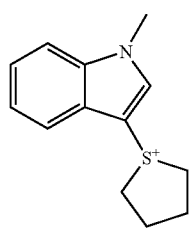
C₄F₉SO₃⁻
(b-60)

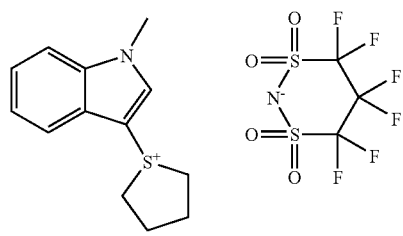
(b-61)

In addition, use may also be made favorably the oxazole derivatives, s-triazine derivatives, and the like, as described in JP-A-2002-122994, paragraph Nos. [0029] to [0030].

Further, use may be also made favorably the onium salt and sulfonate compounds, as exemplified in JP-A-2002-122994, paragraph Nos. [0037] to [0063].

[Polymerization Inhibitor]

In the present invention, a polymerization inhibitor that inhibits the progress of polymerization reactions other than the cationic polymerization is preferably used in combination in order to allow the photocationic polymerization initiator-induced polymerization to proceed effectively.

Preferable examples of the polymerization inhibitor include any compound(s) selected from the group consisting of phenol-series hydroxyl group-containing compounds, quinones, N-oxide compounds, piperidin-1-oxyl free radical compounds, pyrrolidin-1-oxyl free radical compounds, N-nitrosophenylhydroxylamines, and cationic dyes.

Preferable examples of the polymerization inhibitor include hydroquinone, p-methoxyphenol, di-t-butyl-p-cresol, pyrogallol, resorcinol, catechol, t-butylcatechol, hydroquinone, benzoquinone, 4,4-thiobis(3-methyl-6-t-butylphenol), 2,2'-methylene-bis(4-methyl-6-t-butylphenol), 2,2,6,6-tetramethylpiperidine and the derivatives thereof, di-t-butyl nitroxide, 2,2,6,6-tetramethylpiperidine-N-oxide and the derivatives thereof, piperidin-1-oxyl free-radical, 2,2,6,6-tetramethylpiperidin-1-oxyl free radical, 4-oxo-2,2,6,6-tetramethylpiperidin-1-oxyl free radical, 4-hydroxy-2,2,6,6-tetramethylpiperidin-1-oxyl free radical, 4-acetamido-2,2,6,6-tetramethylpiperidin-1-oxyl free radical, 4-maleimido-2,2,6,6-tetramethylpiperidin-1-oxyl free radical, 4-phosphonoxy-2,2,6,6-tetramethylpiperidin-1-oxyl free radical, 3-carboxy-2,2,5,5-tetramethylpyrrolidin-1-oxyl free radical, N-nitrosophenylhydroxylamine cerous salt, N-nitrosophenylhydroxylamine aluminum salt, crystal violet, methyl violet, ethyl violet, and Victoria Pure Blue BOH. The polymerization inhibitor is preferably added in an amount of about 0.01% by mass to about 5% by mass, based on the mass of the total solid of the composition.

[Photosensitizer]

In the present invention, a photosensitizer may be added for the purpose of improving the sensitivity of the photopolymerization initiator. Preferable examples of the photosensitizer include sensitizing dyes belonging to the following compound classes and having absorption wavelengths in the range of 350 to 450 nm: multinuclear aromatics (e.g., pyrene, perylene, and triphenylene), xanthenes (e.g., fluorescein, eosin, erythrosine, rhodamine B, and Rose Bengal), cyanines (e.g., thiacarbocyanine and oxacarbocyanine), merocyanines (e.g., merocyanine and carbomerocyanine), thiazines (e.g., thionine, methylene blue, and toluidine blue), acridines (e.g., acridine orange, chloroflavine, and acriflavine), anthraquinones (e.g., anthraquinone), squariliums (e.g., squariliums), coumarins (e.g., 7-diethylamino-4-methyl coumarin).

More preferable examples of the sensitizing dye include compounds represented by any of formulae (IX) to (XIII):

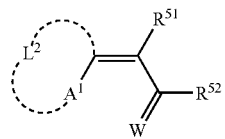
(IX)

-continued

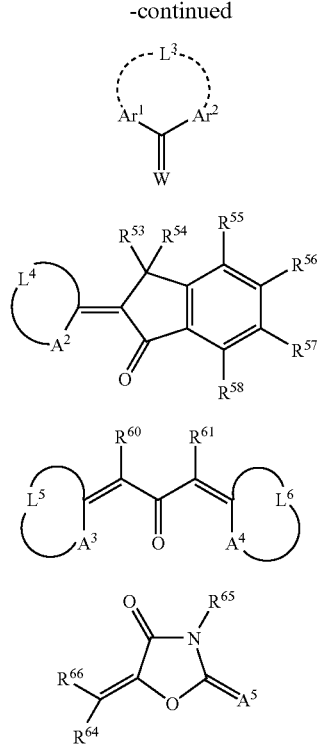

In formula (IX), $A^1$ represents a sulfur atom or $NR^{50}$, $R^{50}$ represents an alkyl group or an aryl group, $L^2$ represents a nonmetallic atomic group which, together with $A^1$ and the carbon atom adjacent thereto, forms a basic nucleus of a dye, $R^{51}$ and $R^{52}$ each independently represent a hydrogen atom or a monovalent nonmetallic atomic group, $R^{51}$ and $R^{52}$ may bond to each other to form an acidic nucleus of a dye, and W represents an oxygen atom or a sulfur atom.

In formula (X), $Ar^1$ and $Ar^2$ each independently represent an aryl group, and bond to each other via a linkage -$L^3$- which represents —O— or —S—. W has the same definition as in formula (IX).

In formula (XI), $A^2$ represents a sulfur atom or $NR^{59}$, $L^4$ represents a nonmetallic atomic group which, together with $A^2$ and the carbon atom adjacent thereto, forms a basic nucleus of a dye, $R^{53}$, $R^{54}$, $R^{55}$, $R^{56}$, $R^{57}$ and $R^{58}$ each independently represent a monovalent nonmetallic atomic group, and $R^{59}$ represents an alkyl group or an aryl group.

In formula (XII), $A^3$ and $A^4$ each independently represent —S— or —$NR^{62}$— or —$NR^{63}$—. $R^{62}$ and $R^{63}$ each independently represent a substituted or unsubstituted alkyl group or a substituted or unsubstituted aryl group. $L^5$ represent a nonmetallic atomic group which, together with $A^3$ and the carbon atom adjacent thereto, forms a basic nucleus of a dye. $L^6$ represent a nonmetallic atomic group which, together with $A^4$ and the carbon atom adjacent thereto, forms a basic nucleus of a dye. $R^{60}$ and $R^{61}$ each independently represent a hydrogen atom or a monovalent nonmetallic atomic group, or $R^{60}$ and $R^{61}$ bond to each other to form an aliphatic or aromatic cycle.

In formula (XIII), $R^{66}$ represents an optionally substituted aromatic cycle or heterocycle, $A^5$ represents an oxygen atom, a sulfur atom, or —$NR^{67}$—. $R^{64}$, $R^{65}$, and $R^{67}$ each independently represent a hydrogen atom or a monovalent nonmetallic atomic group. $R^{67}$ and $R^{64}$ may be bonded to each other to form an aliphatic or aromatic ring. $R^{65}$ and $R^{67}$ may be bonded to each other to form an aliphatic or aromatic cycle.

Preferable examples of the compounds represented by any of formulae (IX) to (XIII) include exemplified compounds (A-1) to (A-20) shown below:

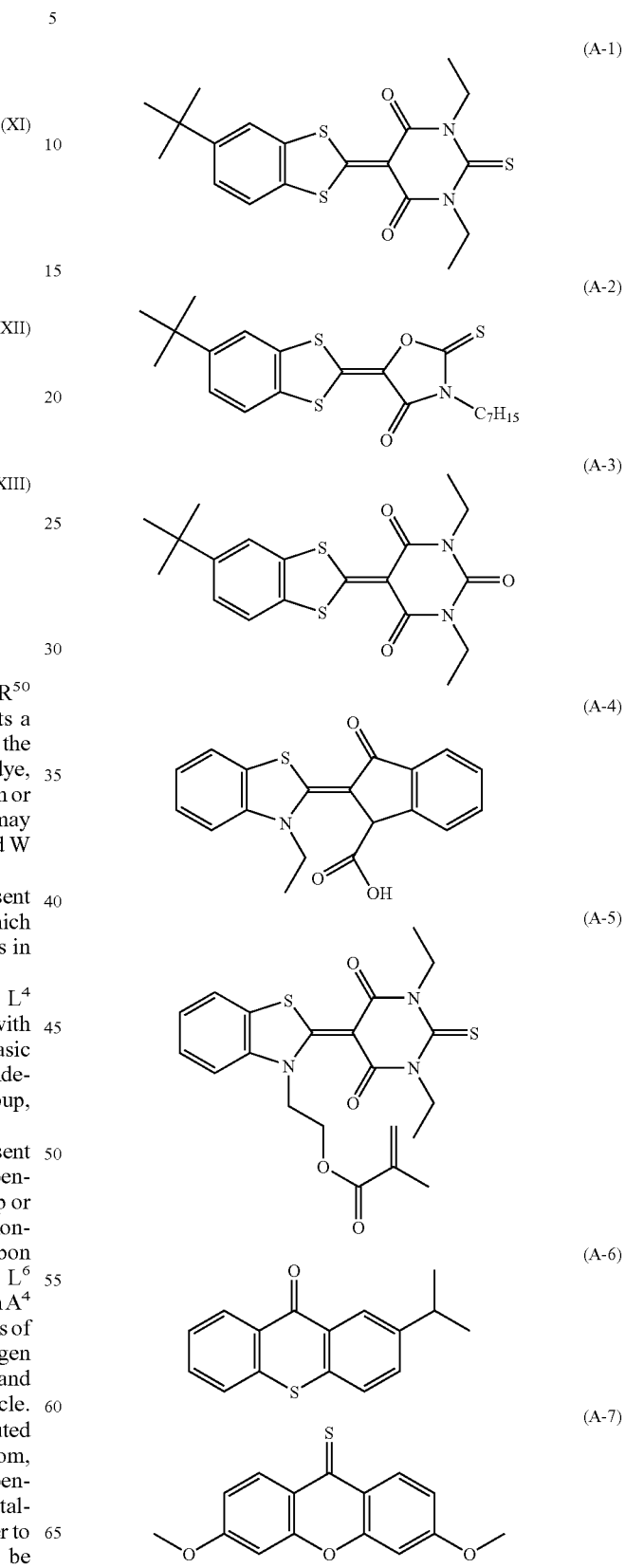

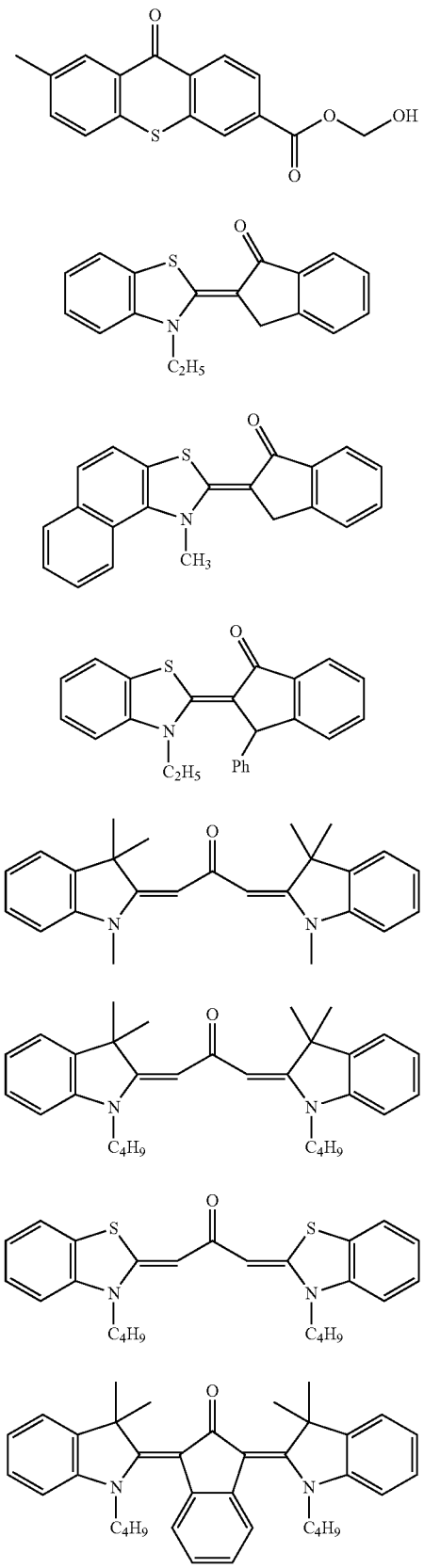
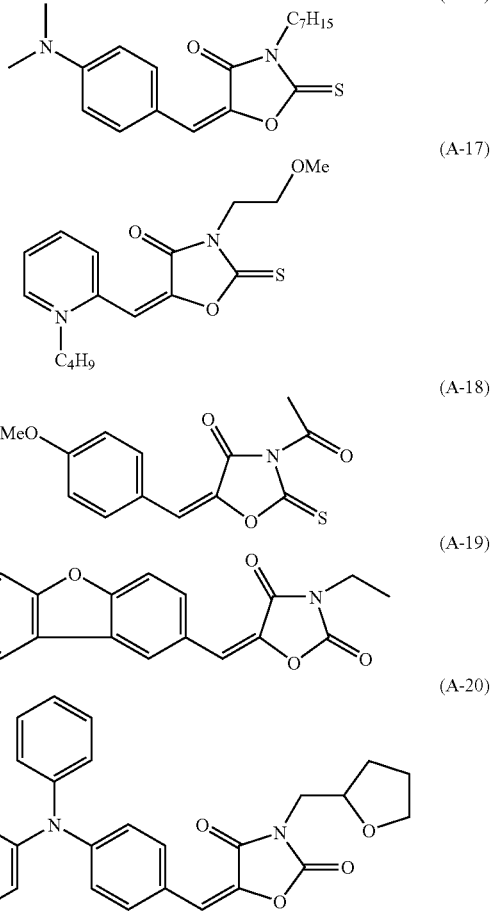

[Colorants]

To the ink composition of the present invention, a colorant for forming a visible image can be preferably added.

The colorant that can be used in the ink composition of the present invention is not particularly limited, and may be selected appropriately from known various colorants (pigments and dyes) to use, according to application. For example, use of a pigment is preferable, for forming an image excellent in weather resistance. As the dye, either a water-soluble dye or an oil-soluble dye may be used, as long as it is a dye soluble in the polymerizable compound. In the present invention, the ink composition of the present invention preferably contains a pigment or an oil-soluble dye, as a colorant, for forming an image or character(s).

The content of the colorant in the ink composition is preferably from 0.5 to 20% by mass, more preferably from 1 to 15% by mass, still more preferably from 5 to 15% by mass.

First, the pigment that can be preferably used as the colorant in the present invention, will be described.

<Pigment>

The pigment is not particularly limited, and use may be made of any of commonly commercially available pigments, including organic and inorganic pigments; dispersions of a pigment dispersed in an insoluble resin, as a dispersant, or the like; and pigments surface-grafted with a resin. Further, resin particles dyed with a dye may also be used.

Examples of such pigments include the pigments described, for example, in, edited by Seijiro Itoh, "Dictionary of Pigments" (2000); W. Herbst, K. Hunger, "Industrial Organic Pigments"; and JP-A-2002-12607, JP-A-2002-188025, JP-A-2003-26978, and JP-A-2003-342503.

Specific examples of the organic or inorganic pigment that can be used in the present invention include:

Yellow-color-forming pigments, including monoazo pigments, such as C.I. Pigment Yellow 1 (Fast Yellow C, etc.) and C.I. Pigment Yellow 74; disazo pigments, such as C.I. Pigment Yellow 12 (Disazo Yellow AAA, etc.) and C.I. Pigment Yellow 17; non-benzidine-series azo pigments, such as C.I. Pigment Yellow 180; azolake pigments, such as C.I. Pigment Yellow 100 (tartrazine yellow lake, etc.); condensation azo pigments, such as C.I. Pigment Yellow 95 (condensation azo yellow GR, etc.); acidic dye lake pigments, such as C.I. Pigment Yellow 115 (quinoline yellow lake, etc.); basic dye lake pigments, such as C.I. Pigment Yellow 18 (thioflavin lake, etc.); anthraquinone-series pigments, such as fravantrone yellow (Y-24); isoindolinone pigments, such as isoindolinone yellow 3RLT (Y-110); quinophtharone pigments, such as quinophtharone yellow (Y-138); isoindoline pigments, such as isoindoline yellow (Y-139); nitroso pigments, such as C.I. Pigment Yellow 153 (nickel nitroso yellow, etc.); metal complex salt azomethine pigments, such as C.I. Pigment Yellow 117 (copper azomethine yellow, etc.), and the like;

Red- or magenta-color-forming pigments, including monoazo-series pigments, such as C.I. Pigment Red 3 (toluidine red, etc.); disazo pigments, such as C.I. Pigment Red 38 (pyrazolone red B, etc.); azolake pigments, such as C.I. Pigment Red 53:1 (lake red C, etc.) and C.I. Pigment Red 57:1 (Brilliant Carmine 6B); condensation azo pigments, such as C.I. Pigment Red 144 (condensation azo red BR, etc.); acidic dye lake pigments, such as C.I. Pigment Red 174 (phloxine B lake, etc.); basic dye lake pigments, such as C.I. Pigment Red 81 (rhodamine 6G' lake, etc.); anthraquinone-series pigments, such as C.I. Pigment Red 177 (dianthraquinonyl red, etc.); thioindigo pigments, such as C.I. Pigment Red 88 (Thioindigo Bordeaux, etc.); perynone pigments, such as C.I. Pigment Red 194 (perynone red, etc.); perylene pigments, such as C.I. Pigment Red 149 (perylene scarlet, etc.); quinacridone pigments, such as C.I. Pigment Violet 19 (unsubstituted quinacridone) and C.I. Pigment Red 122 (quinacridone magenta, etc.); isoindolinone pigments, such as C.I. Pigment Red 180 (isoindolinone red 2BLT, etc.); alizarin lake pigments, such as C.I. Pigment Red 83 (madder lake, etc.), and the like;

Blue- or cyan-color-forming pigments, including disazo-series pigments, such as C.I. Pigment Blue 25 (dianisidine blue, etc.); phthalocyanine pigments, such as C.I. Pigment Blue 15 (phthalocyanine blue, etc.); acidic dye lake pigments, such as C.I. Pigment Blue 24 (peacock blue lake, etc.); basic dye lake pigments, such as C.I. Pigment Blue 1 (Vicrotia Pure Blue BO lake, etc.); anthraquinone-series pigments, such as C.I. Pigment Blue 60 (indanthron blue, etc.); alkali blue pigments, such as C.I. Pigment Blue 18 (alkali Blue V-5:1), and the like;

Green-color-forming pigments, including phthalocyanine pigments, such as C.I. Pigment Green 7 (phthalocyanine green) and C.I. Pigment Green 36 (phthalocyanine green); azo metal complex pigments, such as C.I. Pigment Green 8 (nitroso green), and the like;

Orange-color-forming pigments, including isoindoline-series pigments, such as C.I. Pigment Orange 66 (isoindoline orange); and anthraquinone-series pigments, such as C.I. Pigment Orange 51 (dichloropyranthron orange), and the like; and Black-color-forming pigments, such as carbon black, titanium black, aniline black, and the like.

Further, specific examples of white pigment that can be used include basic lead carbonate $(2PbCO_3Pb(OH)_2$, so-called silver white), zinc oxide (ZnO, so-called zinc white), titanium oxide ($TiO_2$, so-called titanium white), strontium titanate ($SrTiO_3$, so-called titanium strontium white), and the like.

Titanium oxide has a lower specific gravity and a higher refractive index, as compared to other white pigments, and is more stable chemically or physically, and thus has greater masking and/or coloring power as a pigment, and is excellent in resistance to acid or alkali and other environmental factors. Thus, use of titanium oxide as the white pigment is preferable. Off course, another white pigment(s) (including white pigments other than those enumerated in the above) may be used, as needed.

For dispersing the pigment(s), any of dispersing machines may be used, for example, a ball mill, a sand mill, an attriter, a roll mill, a jet mill, a homogenizer, a paint shaker, a kneader, an agitator, a Henschel mixer, a colloid mill, an ultrasonic wave homogenizer, a pearl mill, and a wet jet mill.

It is also possible to add a dispersant, when conducting dispersing of the pigment. Examples of the dispersant include hydroxyl group-containing carboxylic acid esters, salts of a long-chain polyaminoamide with a high-molecular-weight acid ester, high-molecular-weight polycarboxylic acid salts, high-molecular-weight unsaturated acid esters, polymeric copolymers, modified polyacrylates, polyvalent aliphatic carboxylic acids, naphthalenesulfonic acid/formalin condensates, polyoxyethylene alkylphosphoric acid esters, pigment derivatives, and the like. Use of a commercially available polymeric dispersant, e.g. a Solsperse series product (trade name), manufactured by Zeneca, is also preferable.

A dispersing aid suitable to be a synergist to the pigment to be used, may be used. The dispersant and dispersing aid are preferably added in an amount of 1 to 50 parts by mass, to 100 parts by mass of the pigment.

In the ink composition, a solvent may be added as a dispersion medium for various components such as the pigment, or alternatively, without any solvent, the cationically-polymerizable compound above, which is a low-molecular weight component, may be used as a dispersion medium. Contrary to the above, the ink composition of the present invention preferably contains no solvent, since the ink composition of the present invention provides a radiation-curable ink that is to be cured after application on a recording medium (recording material). This is because if a solvent remains in the cured ink image, the remaining solvent leads to deterioration in solvent resistance or causes a problem of volatile organic compounds (VOC) from the remaining solvent. From the viewpoints above, as the dispersion medium, the cationically-polymerizable compound is preferably used, and in particular, it is preferable to choose the cationically polymerizable monomer (compound) having the lowest viscosity, for improving dispersing suitability and handling property of the ink composition.

The finer the average particle diameter of the pigment to be used is, the better the color-forming property is. Thus, the average particle diameter of the pigment is preferably from about 0.01 to about 0.4 μm, more preferably from 0.02 to 0.2 μm. The type of the pigment, the dispersing agent, and the dispersion medium, the dispersing conditions, and the filtration conditions may be selected and determined such that the maximum particle diameter is set at generally 3 μm or less, preferably at 1 μm or less. This particle diameter control can prevent clogging of head nozzles and maintain the storage stability of the ink, the transparency of the ink and the curing sensitivity.

The particle diameter of the pigment in the ink composition may be measured by known measurement methods. Specifically, the measurement may be performed by a centrifugal sedimentation-optical transmission method, an X-ray transmission method, a laser diffraction/scattering method, a dynamic light scattering method, or a counting method with a transmission electron microscope. Specifically, in the present invention, values obtained by a counting method with a transmission electron microscope are adopted.

The content of the pigments in the ink composition is preferably from 1 to 20% by mass, more preferably from 2 to 10% by mass, on solid basis (i.e. in terms of the solid contents).

<Dye>

Next, the dye that can be preferably used as the colorant in the present invention will be described.

The dye to be used may be appropriately selected from known compounds (dyes). Specific examples of the dye include the dyes described in JP-A-2002-114930, in paragraphs [0023] to [0089].

Examples of a yellow dye that can be used include aryl- or heteryl-azo dyes having any of phenols, naphthols, anilines, pyrazolones, pyridones, or open-chain-type active methylene compounds, as a coupling component; azomethine dyes, for example, having an open-chain-type active methylene compound, as a coupling component; methine dyes, such as benzylidene dyes and monomethine oxonol dyes; quinone-series dyes, such as naphthoquinone dyes and anthraquinone dyes; as well as quinophtharone dyes, nitro dyes, nitroso dyes, acridine dyes, and acridinone dyes.

Examples of a magenta dye that can be used include aryl- or heteryl-azo dyes having any of phenols, naphthols, anilines, pyrazolones, pyridones, pyrazolotriazoles, closed-chain-type active methylene compounds (e.g., dimedone, barbituric acid, and 4-hydroxycoumarin derivatives), or electron-excess heterocycles (e.g., pyrrole, imidazole, thiophene, and thiazole derivatives), as a coupling component; azomethine dyes, for example, having any of pyrazolones or pyrazolotriazoles, as a coupling component; methine dyes, such as arylidene dyes, styryl dyes, merocyanine dyes, and oxonol dyes; carbonium dyes, such as xanthene dyes; diphenylmethane dyes; triphenylmethane dyes; quinone-series dyes, such as naphthoquinone, anthraquinone, and anthrapyridone dyes; fused polycyclic dyes, such as dioxazine dyes.

Examples of a cyan dye that can be used include azomethine dyes, such as indoaniline dyes and indophenol dyes; polymethine dyes, such as cyanine dyes, oxonol dyes, and merocyanine dyes; carbonium dyes, such as xanthene dyes; diphenylmethane dyes; triphenylmethane dyes; phthalocyanine dyes; anthraquinone dyes; aryl- or heteryl-azo dyes, for example, having any of phenols, naphthols, anilines, pyrrolopyrimidin-ons or pyrrolotriazine-on derivatives, as a coupling component; and indigo/thioindigo dyes.

The dyes above each may develop a color of yellow, magenta, or cyan, only when a part of the chromophore is dissociated. In such a case, the counter cation may be an inorganic cation, such as an alkali metal, or ammonium; or an organic cation, such as pyridinium or quaternary ammonium salt; or a cationic polymer having such a partial structure.

The dye that can be used in the present invention is preferably soluble in oil. Specifically, the "oil-soluble" dye means a dye having a solubility in water at 25° C. (the mass of the colorant dissolved in 100 g of water) of generally 1 g or less, preferably 0.5 g or less, and more preferably 0.1 g or less. Accordingly, a so-called oil-soluble dye that is insoluble in water can be preferably used.

It is also preferable to introduce an oil-solubilizing group (i.e. a group rendering the dye soluble in an oil) into the basic structure (nuclear) of the dye mentioned in the above that can be used in the present invention, to ensure that the dye is dissolved in a necessary amount in the ink composition.

Examples of the oil-solubilizing group include long-chain branched alkyl groups, long-chain branched alkoxy groups, long-chain branched alkylthio groups, long-chain branched alkylsulfonyl groups, long-chain branched acyloxy groups, long-chain branched alkoxycarbonyl groups, long-chain branched acyl groups, long-chain branched acylamino groups, long-chain branched alkylsulfonylamino groups, and long-chain branched alkylaminosulfonyl groups, as well as aryl, aryloxy, aryloxycarbonyl, arylcarbonyloxy, arylaminocarbonyl, arylaminosulfonyl or arylsulfonylamino groups each containing any of the aforementioned long-chain branched groups.

Alternatively, it is also possible to convert a water-soluble dye containing a carboxylic acid or sulfonic acid group, with a long-chain branched alcohol, amine, phenol, or aniline derivative, thereby to obtain a target dye having an oil-solubilizing group, such as an alkoxycarbonyl, aryloxycarbonyl, alkylaminosulfonyl, or arylaminosulfonyl group.

The oil-soluble dye preferably has a melting point of 200° C. or lower, more preferably 150° C. or lower, and further preferably 100° C. or lower. Use of a low-melting-point oil-soluble dye makes it possible to reduce crystal precipitation of the colorant in the ink composition and improve the storage stability of the resultant ink composition.

Further, the dye preferably has a high oxidation potential (in the noble direction), for improving discoloration resistance, in particular resistance to oxidative materials such as ozone, and curing characteristics. Thus, it is preferable to use the oil-soluble dye that can be used in the present invention having an oxidation potential versus saturated calomel electrode (vs. SCE) of at least 1.0 V. The higher the oxidation potential is, the more preferable it is, and the dye having the oxidation potential of 1.1 V (vs. SCE) or more but 2.0 V or less is more preferable, and the dye having the oxidation potential of 1.15 V (vs. SCE) or more but 2.0 V or less is particularly preferable.

As the yellow color dye, compounds having the structure represented by formula (Y-I), as described in JP-A-2004-250483, are preferable.

Examples of a particularly preferable dye include the dyes represented by any of formulae (Y-II) to (Y-IV), as described in JP-A-2004-250483, paragraph No. [0034], and specific examples thereof include the compounds described in JP-A-2004-250483, paragraph Nos. [0060] to [0071]. The oil-soluble-dyes represented by formula (Y-I) described in the aforementioned publication may be used not only in a yellow ink but also in inks of any other colors, such as a black ink and a red ink.

As the magenta color dye, compounds having the structures represented by formula (3) or (4), as described in JP-A-2002-114930, are preferable; and specific examples thereof include the compounds described in JP-A-2002-114930, paragraph Nos. [0054] to [0073].

Examples of a particularly preferable dye include the azo dyes represented by any of formulae (M-1) to (M-2), as described in JP-A-2002-121414, paragraph Nos. [0084] to [0122], and specific examples thereof include the compounds described in JP-A-2002-121414, paragraph Nos. [0123] to [0132]. The oil-soluble dyes represented by any of formulae (3), (4), and (M-1) to (M-2) described in the aforementioned publication may be used not only in a magenta ink but also in inks of any other colors, such as a black ink and a red ink.

As the cyan color dye, preferable examples include the dyes represented by any of formulae (1) to (IV), as described in JP-A-2001-181547, and the dyes represented by any of formulae (IV-1) to (IV-4), as described in JP-A-2002-121414, paragraph Nos. [0063] to [0078]; and specific examples thereof include the compounds as described in JP-A-2001-181547, paragraph Nos. [0052] to [0066], and in JP-A-2002-121414, paragraph Nos. [0079] to [0081].

Examples of a particularly preferable dye include the phthalocyanine dyes represented by formula (C-I) or (C-II), as described in JP-A-2002-121414, paragraph Nos. [0133] to [0196]; and further preferably the phthalocyanine dyes represented by formula (C-II). Specific examples thereof include the compounds described in JP-A-2002-121414, paragraph Nos. [0198] to [0201]. The oil-soluble dyes represented by any of formulae (I) to (IV), (IV-1) to (IV-4), (C-I), and (C-II) may be used not only in a cyan ink but also in inks of any other colors, such as a black ink and a green ink.

(Oxidation Potential)

The value of oxidation potential (Eox) of the dye that can be used in the present invention, can be readily measured by one skilled in the art. Methods for measuring the oxidation potential are described, for example, by P. Delahay, "New Instrumental Methods in Electrochemistry," 1954, Interscience Publishers; A. J. Bard, et al., "Electrochemical Methods," 1980, John Wiley & Sons; Akira Fujishima, et al., "Denki Kagaku Sokutei-ho (Electrochemical Measuring Methods)", 1984, Gihodo Shuppan Co., Ltd.

Specifically, the oxidation potential may be measured by a process that includes: dissolving a test sample at a concentration of $1 \times 10^{-2}$ to $1 \times 10^{-6}$ mol/liter, in a solvent (e.g. dimethylformamide or acetonitrile) that contains a supporting electrolyte (e.g. sodium perchlorate or tetrapropylammonium perchlorate); and determining the target oxidation potential value relative to a saturated calomel electrode (SCE), by any of various voltammetric methods (e.g. a polarographic method with a dropping mercury electrode, a cyclic voltammetry method, or a method with a rotating disk electrode). The value may deviate to an extent of approximately several dozen millivolts, under the influence of the difference in the voltage between liquids and the resistivity of the sample solution, but it is possible to assure the reproducibility of the electric potential by using a standard sample (e.g., hydroquinone).

Specifically, in the present invention, the oxidation potential of a dye is determined by a process that includes: dissolving the dye at a concentration of 0.001 mol/liter in a N,N-dimethylformamide solvent containing 0.1 mol/liter of tetrapropylammonium perchlorate as a supporting electrolyte; and measuring the target oxidation potential value (vs. SCE) using a saturated calomel electrode (SCE) (reference electrode), a graphite electrode (working electrode), and a platinum electrode (counter electrode).

The value Eox represents the easiness of electron transfer from sample to electrode, and a greater value (higher oxidation potential) indicates that the electron transfer from sample to electrode is more difficult, or in other words it is difficult to oxidize the sample. In relation to the structure of compounds, the introduction of an electron-withdrawing group can make the oxidation potential more electropositive, while the introduction of an electron-donating group can make the oxidation potential more electronegative. In the present invention, it is preferred that an electron-withdrawing group be introduced into the skeleton of a dye to make the oxidation potential more electropositive, such that the reactivity with ozone, an electrophile, can be reduced.

[Other Components]

A description is given below of various additives that may be added as needed, to the ink composition of the present invention.

—Ultraviolet Absorbent—

To the ink composition of the present invention, an ultraviolet absorbent may be added, from the viewpoints of improvement in weather fastness and prevention of discoloration of the image obtained.

Examples of the ultraviolet absorber include so-called fluorescent whitening agents, which are compounds capable of absorbing ultraviolet ray to emit fluorescence, typical examples thereof include compounds as described in Research Disclosure No. 24239, stilbene-series compounds, benzoxazole-series compounds, benzotriazole-series compounds as described in, for example, JP-A-58-185677, JP-A-61-190537, JP-A-2-782, JP-A-5-197075, and JP-A-9-34057, benzophenone-series compounds as described in, for example, JP-A-46-2784, JP-A-5-194483, and U.S. Pat. No. 3,214,463, cinnamic acid-series compounds as described in, for example, JP-B-48-30492 ("JP-B" means examined Japanese patent publication), JP-B-56-21141, and JP-A-10-88106, and triazine-series compounds as described in, for example, JP-A-4-298503, JP-A-8-53427, JP-A-8-239368, JP-A-10-182621, and JP-T-8-501291 ("JP-T" means published searched patent publication).

The addition amount of the ultraviolet absorber may be determined appropriately according to the purposes, and it is generally approximately 0.01 to 10 mass %, to the total amount (total mass) of the ink composition.

—Antioxidant—

To the ink composition, an antioxidant may be added to improve stability. Examples of the antioxidant include those described, for example, in European Patent Publications (Laid-Open) Nos. 223739, 309401, 309402, 310551, 310552, and 459416, German Patent Publications (Laid-Open) No. 3435443, JP-A-54-48535, JP-A-62-262047, JP-A-63-113536, JP-A-63-163351, JP-A-2-262654, JP-A-2-71262, JP-A-3-121449, JP-A-5-61166, JP-A-5-119449, and U.S. Pat. Nos. 4,814,262 and 4,980,275.

The addition amount of the antioxidant may be determined appropriately according to the purposes, and it is generally approximately 0.001 to 1 mass %, to the total amount of the ink composition.

—Discoloration Inhibitor (Anti-fading Agent)—

In the ink composition of the present invention, any one of various organic- or metal complex-series discoloration inhibitors may be used. Examples of the organic anti-fading agent include hydroquinones, alkoxyphenols, dialkoxyphenols, phenols, anilines, amines, indans, chromans, alkoxyanilines, and heterocyclic compounds. Examples of the metal complex-series anti-fading agents include nickel complexes, and zinc complexes. More specific examples of the anti-fading agent that can be used include compounds, as described in patent documents cited in Research Disclosure, No. 17643, Items VII-I to J, ibid., No. 15162, ibid., No. 18716, page 650, left column, ibid., No. 36544, page 527, ibid., No. 307105, page 872, and ibid., No. 15162; and compounds included in compound examples and formulae of typical compounds, as described in JP-A-62-215272, pages 127 to 137.

The addition amount of the anti-fading agent may be determined appropriately according to the purposes, and it is generally approximately 0.001 to 5 mass %, to the total amount of the ink composition.

—Conductive Salts—

To the ink composition of the present invention, a conductive salt, such as potassium thiocyanate, lithium nitrate, ammonium thiocyanate, or dimethylamine hydrochloride, may be added, for controlling the physical properties of the ink ejected.

The addition amount of the conductive salt may be determined appropriately according to the purposes, and it is generally approximately 0.001 to 1.0 mass %, to the total amount of the ink composition.

—Solvent—

To the ink composition of the present invention, addition of an extremely small amount of an organic solvent is also effective, for improving adhesiveness to the recording material or medium.

Examples of the solvent include ketone-series solvents, such as acetone, methyl ethyl ketone, and diethyl ketone; alcohol-series solvents, such as methanol, ethanol, 2-propanol, 1-propanol, 1-butanol, and tert-butanol; chlorine-containing solvents, such as chloroform, and methylene chloride; aromatic-series solvents, such as benzene, and toluene; ester-series solvents, such as ethyl acetate, butyl acetate, and isopropyl acetate; ether-series solvents, such as diethyl ether, tetrahydrofuran, and dioxane; and glycol ether-series solvents, such as ethyleneglycol monomethyl ether, and ethyleneglycol dimethyl ether.

In such a case, the amount of the solvent to be added is effectively within the range that does not cause problems of VOCs and deterioration in solvent resistance, and thus the amount is preferably within the range of 0.1 to 5 mass %, more preferably 0.1 to 3 mass %, to the entire ink composition.

—Polymer Compound—

To the ink composition of the present invention, any of various polymer compounds may be added, for adjusting film physical properties. Examples of the polymer compound that can be used include styrene copolymers, acrylic copolymers, cyclic ether copolymers, polyvinyl butyral resins, polyurethane resins, polyamide resins, polyester resins, epoxy resins, phenol resins, polycarbonate resins, polyvinyl butyral resins, polyvinyl formal resins, shellac, vinyl resins, acrylic resins, rubber-based resins, waxes, and other natural resins. These resins may be used in combination of two or more. In particular, copolymers of a styrene monomer, an acrylic monomer, and a cyclic ether are preferred. Further, as the copolymer unit of the polymer binder, use may also be preferably made of a copolymer comprising a "cyclic ether group-containing monomer" or/and a "vinyl ether group-containing monomer" as a structural unit.

The addition amount of the polymer compound may be determined appropriately according to the purposes, and it is generally approximately 0.01 to 10.0 mass %, to the total amount of the ink composition.

—Surfactant—

Examples of the surfactant include those described in JP-A-62-173463 and JP-A-62-183457. Specific examples thereof include anionic surfactants, such as dialkylsulfosuccinate salts, alkylnaphthalenesulfonate salts, and fatty acid salts; nonionic surfactants, such as polyoxyethylene alkyl ethers, polyoxyethylene alkyl allyl ethers, acetylene glycols, and polyoxyethylene/polyoxypropylene block copolymers; and cationic surfactants, such as alkylamine salts and quaternary ammonium salts. An organofluoro compound may be used in place of the above-described surfactant. The organofluoro compound is preferably hydrophobic. Examples of the organofluoro compound include fluorine-containing surfactants, oily fluorine-containing compounds (e.g., fluorine oil), and solid state fluorine-containing compound resins (e.g., tetrafluoroethylene resins). Examples of the organofluoro compound are described, for example, in JP-B-57-9053 (columns from 8 to 17), and JP-A-62-135826.

The addition amount of the surfactant may be determined appropriately according to the purposes, and it is generally approximately 0.001 to 5.0 mass %, to the total amount of the ink composition.

In addition to the above, to the ink composition of the present invention, may be added, as necessary, for example, a leveling-addition agent, a mat agent, a wax for adjusting the film property; and a tackifier which does not inhibit the polymerization, to improve the adhesiveness onto the recording medium, such as polyolefine or PET.

Specific example of the tackifier include cohesive polymers of high molecular weight, as described in JP-A-2001-49200, pages 5 to 6 (for example, a copolymer comprising an ester of (meth)acrylic acid and an alcohol including an alkyl group having 1 to 20 carbon atoms, an ester of (meth)acrylic acid and an alicyclic alcohol having 3 to 14 carbon atoms, and an ester of (meth)acrylic acid and an aromatic alcohol having 6 to 14 carbon atoms), and tackifying resins of low molecular weight having a polymerizable unsaturated bond.

[Preferred Physical Properties of Ink Composition]

In the case where the ink composition of the present invention is used for inkjet recording, the viscosity of the ink composition is preferably set at 1 to 20 mPa·s, more preferably at 2 to 12 mPa·s, still more preferably at 2 to 10 mPa·s, while the temperature of the ejected ink is kept substantially constant in the range of 15 to 90° C. It is preferred that the composition ratio be adjusted and determined so as to satisfy the above range. The viscosity of the ink at 25° C. is preferably from 1 to 50 mPa·s, more preferably from 2 to 20 mPa·s, still more preferably from 2 to 12 mPa·s.

The surface tension of the ink composition of the present invention is preferably 20 to 30 mN/m, more preferably 23 to 28 mN/m. When the ink composition of the present invention is utilized for recording on any of various recording media composed, for example, of polyolefin, PET, coated paper, or non-coated paper, the surface tension of the ink composition is preferably 20 mN/m or more, from the viewpoints of prevention of ink bleeding and penetration, and it is preferably 30 mN/m or less, from the viewpoints of improvement in wettability.

[Inkjet-recording Method and Inkjet-Recording Device]

The ink composition of the present invention can be preferably used as an ink-jet recording ink. The inkjet-recording method is not particularly limited, and may be any of, for example, an electric charge-control method of ejecting ink, by electrostatic attraction; a drop-on-demand method (pressure pulse method) of using the vibrational pressure of a piezoelectric device; an acoustic inkjet method of ejecting ink, by converting electrical signals into acoustic beams, irradiating the beams on ink, and generating an acoustic radiation pressure in the ink; or a thermal inkjet method of forming air bubbles by heating ink, and using the pressure thus generated. Examples of the inkjet-recording method further include a method of ejecting a so-called photo ink, which is low in concentration, multiple times in droplets in smaller volume; a method of improving image quality, by using multiple inks that are substantially the same in color hue but different in concentration; and a method of using a transparent and colorless ink.

Among the above, the ink composition of the present invention is favorable as an ink for inkjet recoding by a drop-on-demand system (pressure pulse system) using a piezoelectric device.

<Image-forming Method and Recorded Material Resulting from the Same>

The ink composition of the present invention can be used, for example, in an image-forming method comprising: an image-recording step to record an image on a recording material by the inkjet-recording method of ejecting the ink composition of the present invention; or, in an image-forming method comprising: an image-recording step to record an image on a recording material by using the ink composition of the present invention, and an image-curing step to cure the image thus-recorded on the recording material in the image-recording step, by irradiation of active energy ray (active ray). Herein, the "image-recording step" means a image-printing step to print an image on an image-recording material (medium).

In other words, the image-forming method of the present invention may be a method consisting of an image-recording step to form an image by ink-jet recording; or alternatively a method in which the aforementioned method is in combination with an image-curing step. Further, the image-forming method of the present invention may be a method of recording an image in the image-recording step by a method other than ink-jet recording, in combination with the image-curing step.

In the image-curing step according to the present invention, it is possible to form a favorably cured image high in fastness, because, after printing an image on a recording material in the image-printing step, the polymerizable compound, which contributes in imaging, is polymerized and cured progressively, by irradiation of the printed image with active energy ray in the image-curing step.

In the image-curing step, it is possible to conduct exposure to accelerate polymerization and curing of the ink composition, by using a light source that emits an active energy ray having a wavelength region within the range corresponding to the sensitive wavelength of the ink composition. The light source, exposure time period, and light intensity may be selected appropriately, according to the degree of polymerization curing of the polymerizable compound according to the present invention.

The thickness of the image cured in the image-curing step is preferably 2 to 30 μm. The "thickness of an image" means a thickness of a cured product obtained by curing an image which has been formed with the ink composition. By making the thickness of the image within the range of 2 to 30 μm, it is possible to express any image at from a low density to a high density.

The recorded material thus-obtained by using the ink composition of the present invention is cured in the image region by irradiation of ultraviolet ray or the like, and the image region is excellent in strength, and thus, the recorded material may also be used in various applications, for example, as the ink-receiving layer (image region) of planographic printing plate, as well as image-formation using the ink.

Hereinafter, descriptions will be given with respect to the inkjet-recording method and inkjet-recording device, each of which can be preferably used, for example, in the image-recording method of the present invention.

In the inkjet-recording method of the present invention, the recording is performed using the inkjet-recording ink, while any appropriate ink nozzles and the like may be selected and used depending on purposes, without particular limitation thereto. An example of the mode of printing system using the above-described ink may be, but not limited to, one as disclosed in JP-A-2002-11860, but any other mode may also be used.

The inkjet-recording device is typically equipped with means for stabilizing the ink composition temperature, and a section that is to be maintained at a constant temperature includes an ink tank (a middle tank if there is a middle tank) and all pipes and members up to a nozzle discharge surface.

The method for controlling the temperature is not particularly restricted, and it is preferable to control heating according to the ink composition flow rate and the environmental temperature, by providing, for example, a plurality of temperature sensors for each pipe section. Further, a head unit to be heated is preferably thermally shielded or insulated so that the device main body is not influenced by the external temperature. In order to reduce the printer warm-up time required for heating, or in order to reduce the thermal energy loss, it is preferable to thermally insulate the aforementioned section from other sections and also to reduce the heat capacity of the entire heating unit.

Conditions for irradiation with radiation are explained below. A basic irradiation method is disclosed in JP-A-60-132767. Specifically, a light source is provided on either side of a head unit, and the head and the light sources are made to scan by a shuttle system. Irradiation is carried out after a certain period of time has elapsed from when the ink ejected has landed placed on the target. Curing is completed using another light source that is not driven. WO99/54415 discloses, as an irradiation method, a method employing an optical fiber, and a method in which a collimated light source is incident on a mirror surface provided on a head unit side face, and a recording part is irradiated with UV light. In the present invention, any of these irradiation methods may be used. The active energy rays may be radiated, using any of general purpose mercury lamps, metal halide lamps, or any other light source, such as light emitting diodes (LEDs), semiconductor lasers, fluorescent lamps. A light source, electromagnetic waves, or the like capable of promoting the polymerization reaction of the ink may also be used, such as hot cathode ray tubes, cold cathode ray tubes, electron beams, and X rays.

In the present invention, an LED or a semiconductor laser is preferably used as a light source. LEDs or semiconductor lasers are characterized by their small size. In particular, LEDs have the advantages that they have long life, the amount of heat is small, the power consumption is small, ozone is not generated, and they can be used instantly when the power is turned on. A light source at 365 nm±20 nm is advantageous in costs, with which an existing photopolymerization-initiating system may be used.

When a metal halide lamp is used, the lamp to be used is preferably from 10 to 1,000 W/cm$^2$, and the illumination intensity of the medium surface is preferably from 1 mW/cm$^2$ to 100 W/cm$^2$. The exposure energy is preferably from 0.1 mJ/cm$^2$ to 100 J/cm$^2$.

A mercury lamp, a metal halide lamp, or the like, using high voltage discharge, may generate ozone upon electric discharge, and thus it is preferable to equip an exhaust means. The exhaust means is preferably placed such that it can also collect an ink mist generated upon the ejection of the ink.

When curing is performed by radical polymerization, oxygen inhibits the polymerization. Thus, curing may be performed with low energy, by exposure in a low-oxygen-content state, such as a gas atmosphere of nitrogen or the like.

By irradiation of the energy of light or the like for curing to ink-ejection nozzles, an ink mist or some other substance which may adhere onto the nozzle surface be solidified, thereby to interfere with the ejection of the ink. Thus, such means as light shielding is preferably provided, to limit the irradiation to the nozzle as little as possible. Specifically, a partition wall is preferably provided, to prevent the irradiation of nozzle plates; or means for limiting the angle of incidence on the medium is preferably provided, to reduce stray light.

Furthermore, in the present invention, when the ink composition is utilized as an inkjet ink, it is preferable to heat the ink composition to a constant temperature and set the period of time from landing to irradiation at 0.01 to 0.5 sec., and more preferably 0.01 to 0.3 sec., and it is yet more preferable to apply radiation after 0.01 to 0.15 sec. By controlling the time from landing to irradiation in this way so that it is very short, it becomes possible to prevent the landed ink from spreading before curing. Furthermore, since the ink composition can be irradiated to subject to exposure before penetrating deep into a porous recording medium where a light source cannot reach, it is possible to suppress the amount of unreacted monomer remaining, and as a result the odor can be reduced. By using the above-mentioned inkjet-recording method and the ink composition of the present invention, a large synergistic effect can be exhibited. In particular, by using an ink composition having an ink viscosity at 25° C. of 35 to 500 mP·s, a larger effect can be obtained. By employing such a recording method, it is possible to maintain a uniform dot diameter for landed ink even for various types of recording media having different surface wettability, thereby improving the image quality. In order to obtain a color image, it is preferable to superimpose colors in order from those with a low lightness. If an ink having a low lightness is superimposed over another, it is difficult for radiation to reach the lower ink, the curing sensitivity is inhibited, the amount of residual monomer increases, the odor occurs, and the adhesion is apt to deteriorate. Furthermore, although it is possible to discharge all colors and then irradiate them at the same time, it is preferable to irradiate one color at a time from the viewpoint of accelerating the curing of the ink ejected.

The inkjet-recording device that can be used in the present invention is not particularly restricted, and a commercially available inkjet-recording device may be used. That is, in the present invention, recording on a recording medium may be carried out using a commercially available inkjet-recording device.

[Ink-holding Means]

The ink-holding means is preferably a known ink cartridge to fill the ink, and may be the tank placed in a deformable container, as disclosed in JP-A-5-16377. Use of a sub-tank, as disclosed in JP-A-5-16382, stabilizes supply of the ink to an ink head more efficiently. Further, as disclosed in JP-A-8-174860, it is also possible to use a cartridge of a mode to supply ink, by movement of a valve, when the pressure in an ink-supplying chamber declines. Preferable as the method of applying negative pressure to keep the meniscus in the head of the ink-holding means properly, is a method of using the height or head pressure of the ink-holding means, a method of using the capillary force by the filter installed in the ink channel (ink flow path), a method of controlling the pressure by a pump or the like; or a method of holding an ink in an ink-absorber, and applying a negative pressure by the capillary force of the adsorbent for the ink, as disclosed in JP-A-50-74341.

[Ink-supplying Channel]

As a method of supplying the ink from the ink-holding means to a head, the ink-holding means may be connected directly or indirectly via an additional channel, such as a tube, to the head unit. The ink-holding means and channel each are preferably made of a material which has a preferable wettability to the ink, or the ink-holding means and channel are preferably subjected to a surface treatment.

The ink may be ejected, for example, by the method of ejecting ink droplets continuously, and selectively controlling the droplets to reach or not to reach to a medium (a recording material), while deflecting the droplet direction according to the desired image, as disclosed in JP-A-5-104725; or by a so-called on-demand method of ejecting ink droplets only in the region needed for the image. The on-demand method may be the method of ejecting ink, by generating an ink pressure by deformation of a structure by using a piezoelectric device or the like, as disclosed in JP-A-5-16349; or the method of ejecting ink by the pressure caused by expansion of the ink by vaporization by the supplied heat energy, as disclosed in JP-A-1-234255. Alternatively, it may be a method of controlling ejection of ink on a medium under an electric field, as disclosed in JP-A-2001-277466.

Nozzles similar to the mode as described, for example, in JP-A-5-31908, are applicable. The nozzles may be arranged in multiple lines, as described in JP-A-2002-316420, to eject multiple color inks, and thus, it is possible to form a color image at a high speed by using such nozzles, and even faster by installing multiple head units each having nozzles in multiple lines.

It is possible to form an image at high speed, by placing multiple nozzles covering the width equivalent or wider than that of the image, i.e., preparing a so-called line head and conveying the medium simultaneously with ink ejection form these nozzles, as described in JP-A-63-160849. Further, it is possible to prevent adhesion of the ink droplet or adhesion of a portion of the ink droplet flied onto the nozzle surface, by treating the surface of the nozzles in a manner similar to that disclosed in JP-A-5-116327. The nozzles often become stained even if surface-treated as described above, and thus, it is preferable to clean the nozzles with a blade, as disclosed in JP-A-6-71904. The inks in various colors may not necessarily be ejected from nozzles in the same amount, and even a particular ink may not be ejected at all for a long period of time. In such a case, it is preferable to keep the physical properties of ink in the range preferable for stabilizing the meniscus, by ejecting the ink as needed on the region outside the image region and re-supplying new ink into the head, as disclosed in JP-A-11-157102. Even such treatment may result in penetration or generation of air bubbles in the head. In such a case, it is possible to dispose the ink deteriorated in physical properties and also to discharge the bubbles therein to the outside of the head, by withdrawing (aspiration of) the ink compulsory from the outside of the head, as described in JP-A-11-334092. When no ink is ejected for an extended period of time, it is possible to protect the nozzle surface by covering the nozzle surface with a cap, as disclosed in JP-A-11-138830. Further, there may be occasional failure in ink ejection even with these measures. Image printing in the state where no ink is ejected from some of the nozzles leads to troubles such as unevenness of image. For prevention of the troubles, it is effective to take a measure to detect ink ejection failure, as disclosed in JP-A-2000-343686.

In the process of ejecting the ink, the ink temperature is preferably kept constant with a certain accuracy such that its viscosity can be kept constant. Thus, the system is preferably provided with ink temperature-detecting means, ink heating-means, and control means that controls heating in response to the detected ink temperature. Additionally or alternatively, the system is also preferably provided with means that controls the energy applied to ink ejection means, depending on the ink temperature. Superimposed ink ejection, which is made such that the head unit is moved mechanically in one direction and the medium is synchronizedly moved intermittently in the direction perpendicular to that of the head movement, as described in JP-A-6-115099, is effective in overcoming or obfuscating the unevenness of image due to a low accuracy accompanied by intermittent movement of the medium, and thus, in providing a high-quality image. It is possible, then, to set the relationship between the image quality and the recording speed in a suitable range, by properly determining the relationship among the moving speed of head, the moving distance of medium, and the number of nozzles. Alternatively, it is also possible to obtain similar effects, by fixing the head, mechanically moving the medium reciprocally in a certain direction and intermittently in the direction perpendicular thereto.

[System Parameter]

In forming an image, the diameter of the ink droplet reached on the medium is preferably within the range from 10 to 500 μm, and the diameter of the ink droplet upon ejected from the nozzle is preferably within the range from 5 to 250 μm, and the nozzle diameter is preferably within the range from 15 to 100 μm for that purpose. In order to form a certain image, the number of pixels per inch is preferably 50 to 2,400 dpi, and the nozzle density of the head is preferably 10 to 2,400 dpi, for that purpose. Even when the nozzle density of the head is low, it is possible to realize a high-density droplets reached on the medium, by using a head having a large nozzle gap, by placing the heat unit inclined to the conveying direction of the medium or by placing multiple head units staggered from each other. As described above, it is also possible to record a high-density image, by conveying the medium to a certain distance, after each movement of the head at a low nozzle pitch, by moving the head or medium reciprocally, and bringing the ejected ink droplets reach on different positions on the medium.

The amount of the ink droplet ejected and reached on the medium is preferably adjusted to an appropriate amount within the range of from 0.05 to 25 g/m$^2$ for expressing favorable gradation, and it is preferable to control the size and/or number (quantity) of ink droplets ejected from the head for that purpose.

When the distance between the head and the medium is too large, air flow associated with movement of the head or medium disturbs proper flying of the ejected ink droplet, leading to deterioration in the positional accuracy of the ink droplet reaching on the medium. On the other hand, when the distance is too small, the head and the medium may be brought into contact with each other, due to surface irregularity of medium, vibration caused by a conveyer mechanism, or another reason. Thus, the distance is preferably kept approximately within the range of 0.5 to 2 mm.

[Ink Set]

The ink that can be used may be a single color; or the ink may be/have any one, two, or three color(s) of cyan, magenta, and yellow; or the ink may have four colors including black in addition to the above three colors; or the ink may have another color, as called a particular color, other than the above. The colorant may be a dye or a pigment. The order of ejecting these inks is not particularly limited, and the inks may be ejected so that the ink droplets would reach in the order of lightness from the ink lowest in lightness to the ink highest in lightness, or alternatively from highest to lowest in lightness, but it is preferable to eject the inks in the order preferable on the image-recording quality. The image signal to be recorded is preferably processed, for more favorable color reproduction, for example, as described in JP-A-6-210905.

[Recording Medium]

The ink composition of the present invention may be used favorably, for example, in recording/printing images on known recording media.

The recording medium or material, to which the ink composition of the present invention is applicable, is not particularly limited, and examples of the medium to be used include papers, such as common plain paper, coated or non-coated papers, inkjet paper, and electrophotographic common-use paper; and various non-absorptive resin materials for use in so-called soft packaging, and resin films thereof formed in a film shape; and various plastic films, examples thereof include polyethylene terephthalate (PET) film, oriented polystyrene (OPS) film, oriented polypropylene (OPP) film, biaxially-oriented nylon (ONy) film {'Nylon' is a registered trademark, which indicates polyamide}, polyvinyl chloride (PVC) film, polyethylene (PE) film, triacetyl cellulose (TAC) film, and the like. Examples of other plastics for use as the recording medium materials include polycarbonates, acrylic resins, ABS, polyacetals, PVA, rubbers, and the like. In addition, metals, glasses, cloths, and ceramics are also usable as the recording media. It is also possible to use the recording medium described in JP-A-2001-181549 and JP-A-2001-279141, paragraph Nos. [0228] to [0246].

The first embodiment of the present invention contemplates for providing an active energy ray-curable inkjet ink which are excellent in curing property and ejection stability, and which does not cause brittle fracture even folding the resultant image formed from the inkjet ink by recording and curing on a variety of substrates.

Since the active energy ray-curable inkjet ink of the first embodiment of the present invention utilizes the compound having, in its molecule, an oxetane ring and any of dioxolane, dioxane, and dioxepane rings (two oxygen atoms-containing heterocycles) capable of generating a cation by means of an acid, the ink composition thus-provided is particularly excellent in curing property. Further, the ink composition is excellent in flexibility after curing, and the resultant recorded material which is recorded on a film can be prevented from being cracked even when bending deformation is applied thereto.

According to the first embodiment of the present invention, there can be provided an ink composition which can be cured with low exposure energy, which is excellent in ejection stability, and which does not cause brittle fracture even folded the resultant image after curing. There can also be provided an inkjet-recording method and a recorded material, each using such an ink composition. According to the first embodiment of the present invention, therefore, the ink composition is excellent in ejection stability without using any solvent, and it can be used as an inkjet ink to record good-quality characters or image on a recording medium.

The second embodiment of the present invention contemplates for providing an oxetane compound high in reactivity, and for providing an ink composition using the compound, which ink composition is excellent in curing property, and which does not cause brittle fracture even folding the resultant image formed from the ink composition by recording and curing on a variety of substrates.

Since the ink composition of the second embodiment of the present invention utilizes the compound having both an oxetane ring and a bicycloorthoester group in its molecule, the ink composition thus-provided is particularly excellent in curing property. Further, the ink composition is excellent in flexibility after curing, and the resultant recorded material which is recorded on a film can be prevented from being cracked even when bending deformation is applied thereto.

According to the second embodiment of the present invention, there can be provided an ink composition which is excellent in curing property, and which does not cause brittle fracture even folded the resultant image after curing. There can also be provided an inkjet-recording method and a recorded material, each using such an ink composition.

The present invention will be described in more detail based on the following examples, but the invention is not intended to be limited thereto. In the following Examples and Comparative examples, preparation of an ink for inkjet-recording will be described as an example of the ink composition.

EXAMPLES

Example 1

<Preparation of Pigment Dispersion-1>

The pigment and dispersant, as shown in Table 1, were placed in a ball mill, and dispersed for 16 hours, by using zircon beads of diameter 0.6 mm, to give Pigment dispersion-1. The average particle diameter of the pigment particles in the Pigment dispersion-1, as shown in terms of the average in number, was determined, by measuring the length of a longer axis for 100 particles randomly selected, with a transmission electron microscope (TEM), and averaging the lengths thus measured to find said average in number. The results of the measurement are shown in Table 1.

TABLE 1

|  |  | Pigment dispersion-1 |
|---|---|---|
| Pigment (mass %) | Irgalite Blue GLVO (PB-15:4) trade name, manufactured by Ciba Specialty Chemicals Inc. | 20 |
| Polymerizable compound (mass %) | Aronoxetane OXT-221 trade name, manufactured by Toagosei Co., Ltd. | 72 |

TABLE 1-continued

|  |  | Pigment dispersion-1 |
|---|---|---|
| Dispersant (mass %) | Solsperse 28000 trade name, manufactured by The Lubrizol Corporation | 8 |
| Average particle diameter (nm) |  | 80 |

(Preparation of Sample No. 100)

The components shown below were mixed under stirring, and then filtered through a 5.0-μm membrane filter, to give a cyan ink sample (designated to Sample No. 100).

<Components of Ink Composition Sample No. 100>

| Monomer A: an alicyclic epoxy group-containing compound of the formula below (Celloxide 3000, trade name, manufactured by Daicel UCB Co., Ltd.) | 70 g |
|---|---|
| Monomer B: bis(3-ethyl-3-oxetanylmethyl) ether (Aronoxetane OXT-221, trade name, manufactured by Toagosei Co., Ltd.) | 30 g |
| Pigment dispersion: Pigment Dispersion-1 in Table 1 | 10 g |
| Photopolymerization initiator: a mixture of (4-isobutylphenyl)4-methylphenyliodonium hexafluorophosphate and propylene carbonate (Irgacure 250, trade name, manufactured by Ciba Specialty Chemicals Inc.) | 6.0 g |
| Sensitizer: 9,10-dibutoxyanthracene | 3.0 g |
| Surfactant: BYK 307 (trade name, manufactured by BYK Chemie) | 0.2 g |

Celloxide 3000

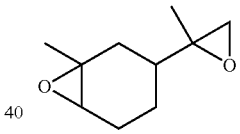

(Preparation of Sample Nos. 101 to 108)

Cyan ink samples (Sample Nos. 101 to 108) were prepared in the same manner as Sample No. 100, except that Monomers A and B were partially changed, as shown in Table 2.

TABLE 2

|  |  |  | Compound C | | Compound D | | |
|---|---|---|---|---|---|---|---|
| Sample No. | Monomer A | Monomer B | Kind | Amount to be added | Kind | Amount to be added | Remarks |
| 100 | 70% | 30% | — | — | — | — | Comparative example |
| 101 | 40% | 40% | I-1 | 20% | — | — | This invention |
| 102 | 40% | 40% | I-3 | 20% |  |  | This invention |
| 103 | 40% | 40% | I-7 | 20% |  |  | This invention |
| 104 | 40% | 40% | I-18 | 20% |  |  | This invention |
| 105 | 40% | 40% | — | — | II-1 | 20% | Comparative example |
| 106 | 40% | 40% |  |  | II-2 | 20% | Comparative example |
| 107 | 35% | 35% | I-1 | 30% |  |  | This invention |
| 108 | 35% | 35% | I-3 | 30% |  |  | This invention |
| 109 | 35% | 35% | I-7 | 30% |  |  | This invention |
| 110 | 35% | 35% | I-18 | 30% |  |  | This invention |
| 111 | 35% | 35% | — | — | II-1 | 30% | Comparative example |
| 112 | 35% | 35% | — | — | II-2 | 30% | Comparative example |

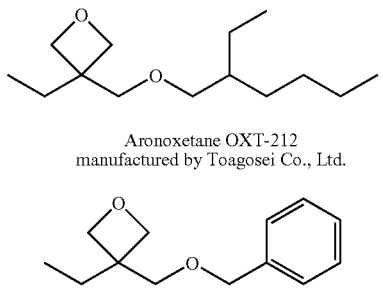

Aronoxetane OXT-212
manufactured by Toagosei Co., Ltd.

<Tests and Evaluation>

1. Printing and Exposure Test

Each of the inks prepared in Examples and Comparative examples was ejected by using a piezoelectric head (Toshiba Tec's print head CA-3 (trade name, manufactured by Toshiba Tec Corporation)). The head 318 nozzles placed at a nozzle density of 150/25.4-mm, and two heads were aligned to dislocate or stagger in a distance of half of the nozzle gap in the nozzle line direction, so that 300 ink droplets per 25.4 mm in the direction of the nozzle line were ejected and reached onto the medium.

The temperature of the head and the liquid ink was kept at 25° C.±1° C., while the ink droplets were ejected. UV light was cut off during the ejection of the ink droplets.

In the Examples and Comparative examples, ink ejection from the head was controlled by the piezoelectric drive signal given to the head, and it was possible to control the volume of an individual droplet to be 6 to 42 μl; and the ink droplet was ejected from the head onto a medium being conveyed at a position 1 mm below the head. The conveying speed was variable to set within the range of 50 to 200 mm/s. The piezoelectric drive frequency was also variable up to 4.6 kHz, and it was possible to control the amount of the ink droplet by these settings. In the Examples and Comparative examples, a contact-printed image (7 cm×12 cm) was obtained, by ejecting the ink droplets in an amount of 10 g/m$^2$, by setting the conveying speed to 90 mm/s and the drive frequency to 1.9 kHz, and controlling the ink ejection quantity to 24 pl.

After ink ejection, the medium was conveyed to an exposure region, where the medium was exposed to the light from an ultraviolet light-emitting diode (UV-LED). The UV-LED used in the Examples and Comparative examples was NCCU033 (trade name, manufactured by Nichia Corporation). The LED emits a UV ray of wavelength 365 nm from one chip, at an output light of approximately 100 mW by application of electric current at approximately 500 mA. The UV-LEDs were aligned with an interval of 7 mm, to give a power of 0.3 W/cm$^2$ on the medium surface. The period of time from ink ejection to exposure and the exposure time period were variable, according to the medium conveying speed and the distance between the head and the LED in the conveying direction. In the Examples and Comparative examples, the exposure to light was conducted approximately 0.5 second after the ejected ink droplets reached on the medium.

It was possible to adjust the exposure energy on the medium within the range of 0.01 to 15 J/cm$^2$, according to the settings of the conveying speed of and the distance with the medium. In the Examples and Comparative examples, the exposure energy was adjusted according to the conveying speed.

The exposure power and the exposure energy were determined as an integral value in the wavelength range of 220 to 400 nm measured by using Spectroradiometer URS-40D (trade name) manufactured by Ushio Inc.

In the Examples and Comparative examples, a PET film of thickness 100 μm and size 8 cm×15 cm was used as a medium, and the printing and exposure tests were conducted in an environment at 23° C. and 60% RH. The thus-cured images each had a thickness of 9 μm.

2. Evaluation of Curing Property

Immediately after the exposure, a sheet of free sheet (wood-free paper) was placed on the thus-printed sample, and the resultant laminate was allowed to pass through pressure rollers (50 kg/cm$^2$), and then the degree of transfer of the colorant to the free sheet was evaluated as shown below. The results of the evaluation are shown in Table 3.

○: No transfer occurred at all.

Δ: Partial transfer occurred.

x: Almost the whole quantity was transferred.

3. Evaluation of Ejection Performance of Nozzles

A grid line image (nozzle check pattern) was printed on the following medium for 1 hour under the same conditions as those for printing in the above '1. Printing and exposure test', except that the medium was changed to an inkjet paper sheet ("Gasai" gloss finished, manufactured by Fuji Photo Film Co., Ltd.). The grid line images at the start of the printing and after the continuous 1-hour printing were observed and compared with each other, and the number of nozzles clogged or nozzles from which the ejection direction was conspicuously deviated was counted after the continuous 1-hour printing. The ejection failure rate (%) of the print head nozzles was calculated as the percentage ratio of the number of ejection failure nozzles to the total number of nozzles (318), to evaluate the defective ejection from the nozzles. The results of the evaluation are shown in Table 3.

○: Ejection from 0 to 5% of the print head nozzles failed.

Δ: Ejection from more than 5% and not more than 20% of the print head nozzles failed.

x: Ejection from more than 20% of the print head nozzles failed.

4. Evaluation of Resistance to Folding of Cured Film

With respect to each ink in the Examples and Comparative examples, the printed sample from which no transfer occurred with the lowest energy was allowed to stand under the conditions of 23° C. and relative humidity 60% for one day, and then folded to 180° by hands at the center part of the image, to observe whether cracking of the cured film was seen or not, in the criteria as shown below. The results of the evaluation are shown in Table 3.

○: There was no change.

Δ: The printed product was slightly cracked at the folded portion.

x: The cured film of the printed product was peeled off at the folded portion.

The results of the evaluation are summarized below with respect to Cyan Ink Sample Nos. 100 to 112.

TABLE 3

| Ink composition sample number | Curing property (Exposure energy: mJ/cm$^2$) 20 | 25 | 30 | 50 | 100 | Folding resistance | Ejection stability | Remarks |
|---|---|---|---|---|---|---|---|---|
| 100 | x | x | x | x | o | x | x | Comparative example |
| 101 | Δ | o | o | o | o | o | o | This invention |
| 102 | Δ | o | o | o | o | o | o | This invention |
| 103 | Δ | o | o | o | o | o | o | This invention |
| 104 | Δ | o | o | o | o | o | o | This invention |
| 105 | Δ | Δ | o | o | o | o | Δ | Comparative example |
| 106 | Δ | Δ | o | o | o | o | x | Comparative example |
| 107 | Δ | o | o | o | o | o | o | This invention |
| 108 | Δ | o | o | o | o | o | o | This invention |
| 109 | Δ | o | o | o | o | o | o | This invention |
| 110 | Δ | o | o | o | o | o | o | This invention |
| 111 | Δ | Δ | o | o | o | o | Δ | Comparative example |
| 112 | Δ | Δ | o | o | o | o | x | Comparative example |

As is apparent from the results shown in Table 3, Sample No. 100 of the comparative example was not sufficiently cured with an exposure energy of 50 mJ/cm$^2$ or less, and caused peeling off of the cured film in the folding test. Sample Nos. 105, 106, 111, and 112 of the comparative examples had folding resistance, but were not sufficiently cured with an exposure energy of 25 mJ/cm$^2$ or less and were insufficient in ejection stability. Contrary to the above, it was demonstrated that Sample Nos. 101 to 104 and 107 to 110, each of which was the ink composition of the first embodiment of the present invention, were cured even with low exposure energy from the light-emitting diode, caused no brittle fracture even folding after the curing, and were excellent in ejection stability.

Example 2

<Preparation of Pigment Dispersion-2>

Pigment dispersion-2 was prepared in the same manner as Pigment dispersion-1 in the above Example 1, except that the average particle diameter of pigment particles in the Pigment dispersion-2 prepared would be 82 nm.

(Preparation of Sample No. 2100)

Cyan ink sample (Sample No. 2100) was prepared in the same manner as the cyan ink Sample No. 100 in the above Example 1, except that the Pigment dispersion-1 (Table 1) was replaced with the same mass of the Pigment dispersion-2.

(Preparation of Sample Nos. 2101 to 2107)

Cyan ink samples (Sample Nos. 2101 to 2107) were prepared in the same manner as Sample No. 2100, except that Monomers A and B were partially changed, as shown in Table 4.

TABLE 4

| Sample No. | Monomer A | Monomer B | Compound C Kind | Compound C Amount to be added | Compound D Kind | Compound D Amount to be added | Remarks |
|---|---|---|---|---|---|---|---|
| 2100 | 70% | 30% | — | — | — | — | Comparative example |
| 2101 | 50% | 30% | 2-I-1 | 20% | — | — | This invention |
| 2102 | 50% | 30% | 2-I-2 | 20% | — | — | This invention |
| 2103 | 40% | 40% | — | — | II-1 | 20% | Comparative example |
| 2104 | 40% | 40% | 2-I-1 | 10% | II-1 | 10% | This invention |
| 2105 | 40% | 40% | 2-I-2 | 10% | II-1 | 10% | This invention |
| 2106 | 40% | 40% | 2-I-1 | 20% | — | — | This invention |
| 2107 | 40% | 40% | 2-I-2 | 20% | — | — | This invention |

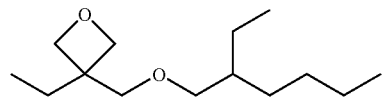

Aronoxetane OXT-212 manufactured by Toagosei Co., Ltd.

II-1

<Test and Evaluation>

2-1. Printing and Exposure Test

The printing and exposure test was conducted in the same manner as in the above Example 1, excepted that UV-light cutting was not conducted in the inkjet droplet ejection, and that the inks as prepared in Examples and Comparative examples as shown in the following Table 4 were utilized in place of those in Table 2.

2-2. Evaluation of Curing Property

The curing property was tested and evaluated in the same manner as in the Example 1 above. The results of the evaluation are shown in Table 5.

2-3. Evaluation of Resistance to Folding of Cured Film

The resistance to folding of the thus-cured film was tested and evaluated in the same manner as in the Example 1 above. The results of the evaluation are shown in Table 5.

TABLE 5

| Ink composition sample number | Curing property (Exposure energy: mJ/cm²) | | | | | Folding resistance | Remarks |
|---|---|---|---|---|---|---|---|
| | 15 | 20 | 25 | 30 | 50 | | |
| 2100 | x | x | x | x | x | x | Comparative example |
| 2101 | Δ | Δ | ○ | ○ | ○ | ○ | This invention |
| 2102 | Δ | Δ | ○ | ○ | ○ | ○ | This invention |
| 2103 | Δ | Δ | Δ | ○ | ○ | ○ | Comparative example |
| 2104 | Δ | ○ | ○ | ○ | ○ | ○ | This invention |
| 2105 | Δ | ○ | ○ | ○ | ○ | ○ | This invention |
| 2106 | Δ | Δ | ○ | ○ | ○ | ○ | This invention |
| 2107 | Δ | Δ | ○ | ○ | ○ | ○ | This invention |

As is apparent from the results shown in Table 5, Sample No. 2100 of the comparative example was low in curing property (which required an energy of 100 mJ/cm² or more for curing the ink), and was also low in folding resistance. Sample No. 2103 of the comparative example was improved in folding resistance, but was insufficient in curing property.

Contrary to the above, each of the samples according to the second embodiment of the present invention was quite high in the ink curing property and good in the folding resistance. In particular, it was demonstrated that Sample Nos. 2104 and 2105, each of which contained, in addition to the cationically-polymerizable compound having both of an oxetane ring and a bicycloorthoester ring in its molecule, another oxetane ring-containing compound, caused no transferring of the image at all even with irradiation energy 20 mJ/cm², and exhibited the ink curing property further improved.

Having described our invention as related to the present embodiments, it is our intention that the invention not be limited by any of the details of the description, unless otherwise specified, but rather be construed broadly within its spirit and scope as set out in the accompanying claims.

This non-provisional application claims priority under 35 U.S.C. §119 (a) on Patent Application No. 2006-206308 filed in Japan on Jul. 28, 2006, and Patent Application No. 2006-206324 filed in Japan on Jul. 28, 2006, each of which is entirely herein incorporated by reference.

What we claim is:

1. An active energy ray-curable ink composition, comprising a compound having, in its molecule, one oxetane ring and at least one selected from a dioxolane ring, a dioxane ring, and a dioxepane ring.

2. The active energy ray-curable ink composition according to claim 1, further comprising any one of an oxirane ring-containing compound or an oxetane ring-containing compound.

3. The active energy ray-curable ink composition according to claim 1, further comprising at least one polymerization initiator and at least one photosensitizer.

4. The active energy ray-curable ink composition according to claim 1, whose viscosity at 25° C. is 2 to 20 mPa·s.

5. An inkjet ink, comprising the active energy ray-curable ink composition according to claim 1.

6. An image-forming method, comprising:
an image-recording step to record an image by inkjet-recording of ejecting the active energy ray-curable inkjet ink according to claim 5.

7. The image-forming method according to claim 6, which comprises:
the image-recording step of recording said image on a recording material with the active energy ray-curable inkjet ink; and an image-curing step of curing the image recorded on the recording material in the image-recording step by irradiating the image with an active energy ray.

8. The image-forming method according to claim 7, wherein a light-emitting diode or a semiconductor laser is a light source for the irradiation with the active energy ray.

9. The image-forming method according to claim 7, wherein the central wavelength of the active energy ray is 365±20 nm.

10. The image-forming method according to claim 7, wherein the thickness of the image cured in the image-curing step is 2 to 30 μm.

11. A recorded material, which is formed by using the active energy ray-curable inkjet ink according to claim 5.

12. An ink composition, comprising a cationically-polymerizable compound having, in its molecule, both an oxetane ring and a bicycloorthoester ring.

13. The ink composition according to claim 12, wherein the cationically-polymerizable compound is a compound having one oxetane ring and one bicycloorthoester ring in its molecule.

14. The ink composition according to claim 12, wherein the cationically-polymerizable compound is a compound in which one oxetane ring and one bicycloorthoester ring are linked together via an ether bond.

15. The ink composition according to claim 12, further comprising any one of an oxirane ring-containing compound or an oxetane ring-containing compound.

16. The ink composition according to claim 12, further comprising at least one polymerization initiator and at least one photosensitizer.

17. The ink composition according to claim 12, whose viscosity at 25° C. is 2 to 20 mPa·s.

18. An inkjet-recording ink, comprising the ink composition according to claim 12.

19. An image-forming method, comprising:
an image-recording step to record an image by inkjet-recording of ejecting the inkjet-recording ink according to claim 18.

20. The image-forming method according to claim 19, which comprises:
the image-recording step of recording said image on a recording material with the inkjet-recording ink; and an image-curing step of curing the image recorded on the recording material in the image-recording step by irradiating the image with an active energy ray.

21. The image-forming method according to claim 20, wherein a light-emitting diode or a semiconductor laser is a light source for the irradiation with the active energy ray.

22. The image-forming method according to claim 20, wherein the central wavelength of the active energy ray is 365±20 nm.

23. The image-forming method according to claim 20, wherein the thickness of the image cured in the image-curing step is 2 to 30 μm.

24. A recorded material, which is formed by using the inkjet-recording ink according to claim 18.

25. The active energy ray-curable ink composition according to claim 1, wherein the compound having one oxetane ring and at least one selected from a dioxolane ring, dioxane ring, dioxepane ring is a compound represented by formula (I), (II), or (III):

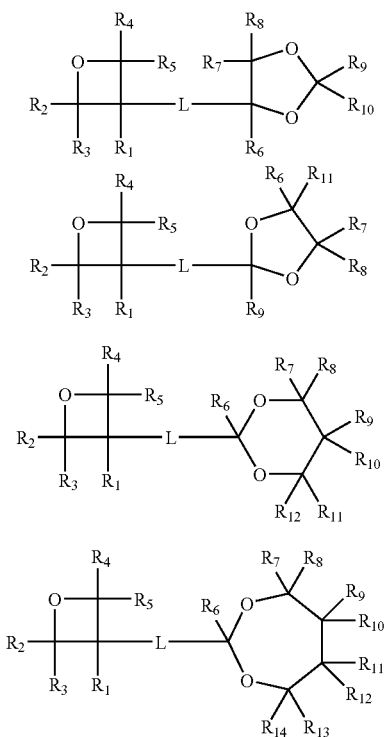

Formula (I)

Formula (II)

Formula (III)

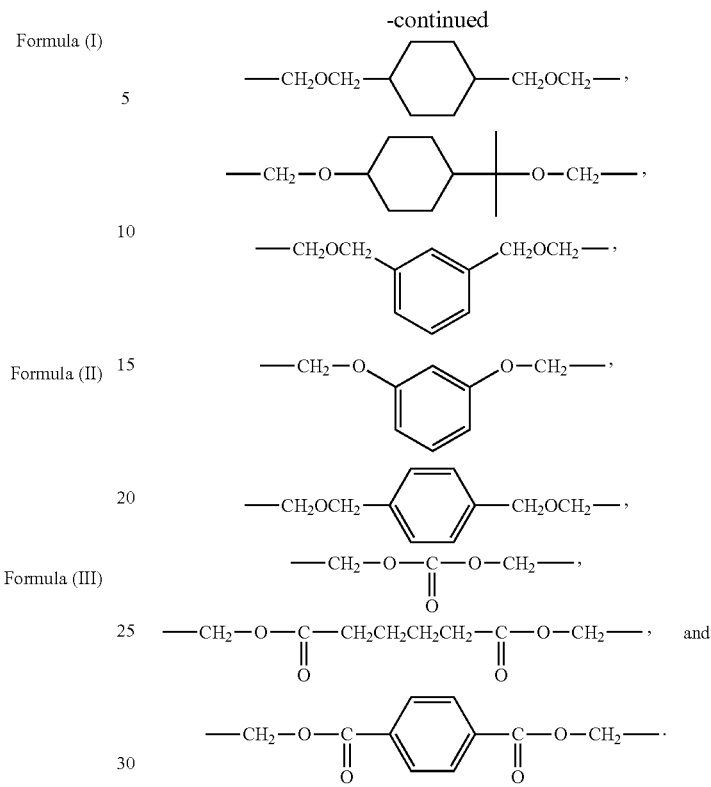

wherein $R_1$ to $R_{14}$ each independently represent a hydrogen atom or a substituent selected from an alkyl group, an alkenyl group, an alkynyl group, an aromatic hydrocarbon group, a heteroaromatic group, a heterocyclic group, an alkoxy group, an aryloxy group, an alkylthio group, an arylthio group, an alkoxycarbonyl group, an aryloxycarbonyl group, a sulfamoyl group, an acyl group, an acyloxy group, an amido group, a carbamoyl group, a ureido group, an alkylsulfonyl group, an arylsulfonyl group, an amino group, a halogen atom, a fluorinated hydrocarbon group, a cyano group, a nitro group, a hydroxy group, a mercapto group, and a silyl group; and L represents a divalent linking group selected from —(CH$_2$)$_2$—, —(CH$_2$)$_3$—, —(CH$_2$)$_4$—, —(CH$_2$)$_6$—, —(CH$_2$)$_8$—, —(CH$_2$)$_{12}$—, —CH$_2$OCH$_2$—, —CH$_2$CH$_2$OCH$_2$CH$_2$—, —CH$_2$OCH$_2$CH$_2$OCH$_2$—, —CH$_2$OCH$_2$CH$_2$CH$_2$OCH$_2$—, —CH$_2$OCH$_2$CH$_2$CH$_2$CH$_2$OCH$_2$—, —CH$_2$OCH$_2$CH$_2$CH$_2$CH$_2$CH$_2$CH$_2$CH$_2$CH$_2$OCH$_2$—, —CH$_2$OCH$_2$CH$_2$OCH$_2$CH$_2$OCH$_2$—, —CH$_2$OCH(CH$_3$)CH$_2$OCH$_2$—, —CH$_2$OCH(CH$_3$)CH$_2$OCH(CH$_3$)CH$_2$OCH$_2$—, —CH$_2$OCH(CH$_3$)CH$_2$CH$_2$OCH$_2$—, —CH$_2$OCH(CH$_3$)CH$_2$CH$_2$CH$_2$OCH$_2$—, —CH$_2$OCH$_2$C(CH$_3$)$_2$CH$_2$OCH$_2$—, —CH$_2$OCH$_2$CH=CHCH$_2$OCH$_2$—, —CH$_2$OCH$_2$CH=C(CH$_3$)CH$_2$CH$_2$CH=C(CH$_3$)CH$_2$OCH$_2$—, —CH$_2$SCH$_2$—, —CH$_2$OCH$_2$CH$_2$SCH$_2$CH$_2$OCH$_2$—,

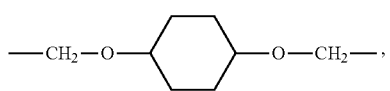

26. The ink composition according to claim 12, wherein the cationically-polymerizable compound is a compound represented by formula (2-I):

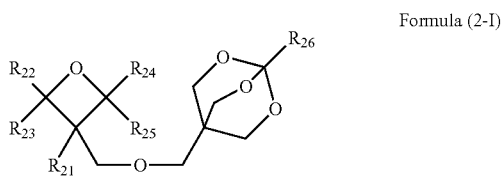

Formula (2-I)

wherein $R_{21}$ to $R_{26}$ each independently represent a hydrogen atom or a substituent selected from an alkyl group, an alkenyl group, an alkynyl group, an aromatic hydrocarbon group, a heteroaromatic group, a heterocyclic group, an alkoxy group, an aryloxy group, an alkylthio group, an arylthio group, an alkoxycarbonyl group, an aryloxycarbonyl group, a sulfamoyl group, an acyl group, an acyloxy group, an amido group, a carbamoyl group, a ureido group, an alkylsulfonyl group, an arylsulfonyl group, an amino group, a halogen atom, a fluorinated hydrocarbon group, a cyano group, a nitro group, a hydroxy group, a mercapto group, and a silyl group.

27. The ink composition according to claim 26, wherein the compound represented by formula (2-I) is a compound represented by formula (2-II):

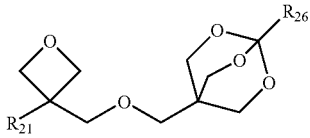

Formula (2-II)

wherein $R_{21}$ and $R_{26}$ each independently represent a hydrogen atom or a substituent selected from an alkyl group, an alkenyl group, an alkynyl group, an aromatic hydrocarbon group, a heteroaromatic group, a heterocyclic group, an alkoxy group, an aryloxy group, an alkylthio group, an arylthio group, an alkoxycarbonyl group, an aryloxycarbonyl group, a sulfamoyl group, an acyl group, an acyloxy group, an amido group, a carbamoyl group, a ureido group, an alkylsulfonyl group, an arylsulfonyl group, an amino group, a halogen atom, a fluorinated hydrocarbon group, a cyano group, a nitro group, a hydroxy group, a mercapto group, and a silyl group.

* * * * *